(12) United States Patent
Vaughan

(10) Patent No.: US 7,645,280 B2
(45) Date of Patent: *Jan. 12, 2010

(54) VERTEBRAL STABILIZATION ASSEMBLY AND METHOD

(75) Inventor: Paul A. Vaughan, Dallas, TX (US)

(73) Assignee: Vaughan Medical Technologies, Inc., Dallas, TX (US)

( * ) Notice: Subject to any disclaimer, the term of this patent is extended or adjusted under 35 U.S.C. 154(b) by 288 days.

This patent is subject to a terminal disclaimer.

(21) Appl. No.: 11/146,075

(22) Filed: Jun. 7, 2005

(65) Prior Publication Data
US 2005/0240183 A1    Oct. 27, 2005

Related U.S. Application Data

(60) Continuation of application No. 11/086,834, filed on Mar. 22, 2005, which is a division of application No. 10/109,172, filed on Mar. 28, 2002, now Pat. No. 6,899,714.

(60) Provisional application No. 60/327,118, filed on Oct. 3, 2001, provisional application No. 60/350,259, filed on Nov. 2, 2001, provisional application No. 60/331,857, filed on Nov. 20, 2001, provisional application No. 60/353,691, filed on Jan. 31, 2002.

(51) Int. Cl.
*A61F 5/00* (2006.01)
*A61B 17/70* (2006.01)

(52) U.S. Cl. ............... 606/86 A; 606/264; 606/279

(58) Field of Classification Search ............ 606/61, 606/96, 97, 98, 102, 104, 72, 86 A, 264, 279
See application file for complete search history.

(56) References Cited

U.S. PATENT DOCUMENTS 4,611,581 A    9/1986  Steffee ................... 128/69

(Continued)

FOREIGN PATENT DOCUMENTS

WO    WO 03/028538 A2    4/2003

(Continued)

OTHER PUBLICATIONS

Gerald E. Rodts, Jr., M.D., *What Should I Know About Lumbar Fusion?* (article found at the Internet Website: www.spineuniverse.com/surgery/specialist/feature0130.html), dated Mar. 28, 2001, 3 pgs.

(Continued)

*Primary Examiner*—Pedro Philogene
(74) *Attorney, Agent, or Firm*—Hunton & Williams LLP

(57) ABSTRACT

A vertebral stabilization assembly for stabilizing vertebrae is provided. The vertebral stabilization assembly includes a first and a second pedicle screw, a first and second connecting screw, and a connecting member. The first and second pedicle screws each have a shaft provided with a threaded portion operable for threading engagement of the first and second pedicle screws with a first and second vertebra, respectively, each shaft also has an engaging portion. The first and second connecting screws each have a first end adapted to be received by the engaging portions of the first and second pedicle screws, respectively. The connecting member has a first end connected to the first connecting screw and a second end connected to the second connecting screw for stabilization of the first and second vertebra. A guide member for placement of the connecting screw and method for anteriorly stabilizing vertebrae is also provided.

16 Claims, 11 Drawing Sheets

U.S. PATENT DOCUMENTS

| | | | |
|---|---|---|---|
| 4,648,388 A | 3/1987 | Steffee | 128/69 |
| 4,655,199 A | 4/1987 | Steffee | 128/69 |
| 4,696,290 A | 9/1987 | Steffee | 128/69 |
| 4,719,905 A | 1/1988 | Steffee | 128/69 |
| 4,722,331 A * | 2/1988 | Fox | 606/96 |
| 4,771,767 A | 9/1988 | Steffee | 128/69 |
| 4,854,311 A | 8/1989 | Stefeee | 128/92 YM |
| 5,005,562 A | 4/1991 | Cotrel | 128/69 |
| 5,092,866 A | 3/1992 | Breard et al. | 606/61 |
| 5,180,381 A | 1/1993 | Aust et al. | 606/61 |
| 5,478,341 A * | 12/1995 | Cook et al. | 606/62 |
| 5,486,176 A | 1/1996 | Hildebrand et al. | 606/71 |
| 5,496,322 A | 3/1996 | Mathews | 606/61 |
| 5,569,248 A | 10/1996 | Mathews | 606/61 |
| 5,584,834 A | 12/1996 | Errico et al. | 606/61 |
| 5,603,713 A | 2/1997 | Aust et al. | 606/61 |
| 5,620,443 A | 4/1997 | Gertzbein et al. | 606/61 |
| 5,681,311 A | 10/1997 | Foley et al. | 606/61 |
| 5,683,391 A | 11/1997 | Boyd | 606/61 |
| 5,728,097 A | 3/1998 | Mathews | 606/61 |
| 5,776,135 A | 7/1998 | Errico et al. | 606/61 |
| 5,814,046 A | 9/1998 | Hopf | 606/61 |
| 5,843,082 A | 12/1998 | Yuan et al. | 606/61 |
| 5,876,402 A | 3/1999 | Errico et al. | 606/61 |
| 5,904,683 A | 5/1999 | Pohndorf et al. | 606/61 |
| 5,947,967 A | 9/1999 | Barker | 606/61 |
| 5,976,135 A | 11/1999 | Sherman et al. | 606/61 |
| 6,030,389 A | 2/2000 | Wagner et al. | 606/71 |
| 6,056,749 A | 5/2000 | Kuslich | 606/61 |
| 6,063,089 A | 5/2000 | Errico et al. | 606/61 |
| 6,066,140 A | 5/2000 | Gertzbein et al. | 606/61 |
| 6,083,224 A | 7/2000 | Gertzbein et al. | 606/61 |
| 6,106,527 A | 8/2000 | Wu et al. | 606/61 |
| 6,132,434 A | 10/2000 | Sherman et al. | 606/78 |
| 6,136,001 A | 10/2000 | Michelson | 606/61 |
| 6,136,002 A | 10/2000 | Shih et al. | 606/61 |
| 6,136,003 A | 10/2000 | Hoeck et al. | 606/61 |
| 6,139,551 A | 10/2000 | Michelson et al. | 606/79 |
| RE37,005 E | 12/2000 | Michelson et al. | 606/99 |
| 6,156,037 A | 12/2000 | LeHuec et al. | 606/61 |
| 6,167,145 A | 12/2000 | Foley et al. | 382/128 |
| 6,187,005 B1 | 2/2001 | Brace et al. | 606/61 |
| 6,190,388 B1 | 2/2001 | Michelson et al. | 606/61 |
| 6,193,721 B1 | 2/2001 | Michelson | 606/70 |
| RE37,161 E | 5/2001 | Michelson et al. | 606/61 |
| 6,228,085 B1 | 5/2001 | Theken et al. | 606/61 |
| 6,235,034 B1 | 5/2001 | Bray | 606/71 |
| 6,669,698 B1 * | 12/2003 | Tromanhauser et al. | 606/61 |
| 2003/0065329 A1 | 4/2003 | Vaughan | |
| 2004/0193161 A1 | 9/2004 | Vaughan | |
| 2004/0254578 A1 | 12/2004 | Vaughan | |

FOREIGN PATENT DOCUMENTS

| | | |
|---|---|---|
| WO | WO 03/028538 A3 | 4/2003 |
| WO | PCT/US2005/11742 | 4/2005 |

OTHER PUBLICATIONS

Charles V. Burton, M.D., *The Present Role of Titanium Cage Fusions In Spine Care*, (article found at the Internet website: www.spineuniverse.com/surgery/procedures/cage2fusion.html), dated Mar. 28, 2001, 3 pgs.

Mark R. McLaughlin, M.D., *Image-Guided Spinal Surgery*, (article found at the Internet website: www.spineuniverse.com/technology/ak_mclaughlin_image-guided.html), dated Mar. 28, 2001, 2 pgs.

*Spine Fusion Surgery—Bone Growth Stimulators* (article found at the Internet website: www.orthofix.com/QFProd/ofsite/T112100c.htm), dated Mar. 28, 2001, 4 pgs.

Dr. Glenn M. Amundson, *Low Back Pain* (article found at the Internet website: www.spineuniverse.com/conditions/detail/lowback_amundson.html), dated Mar. 28, 2001, 4 pgs.

Vaughan, Paul A., Vertebral Stabilization Assembly and Method, U.S. Appl. No. 11/086,834, filed Mar. 22, 2005.

Vaughan, Paul A., Vertebral Stabilization Assembly and Method With Rigid & Semi-Rigid Members, U.S. Appl. No. 11/185,793, filed Jul. 21, 2005.

* cited by examiner

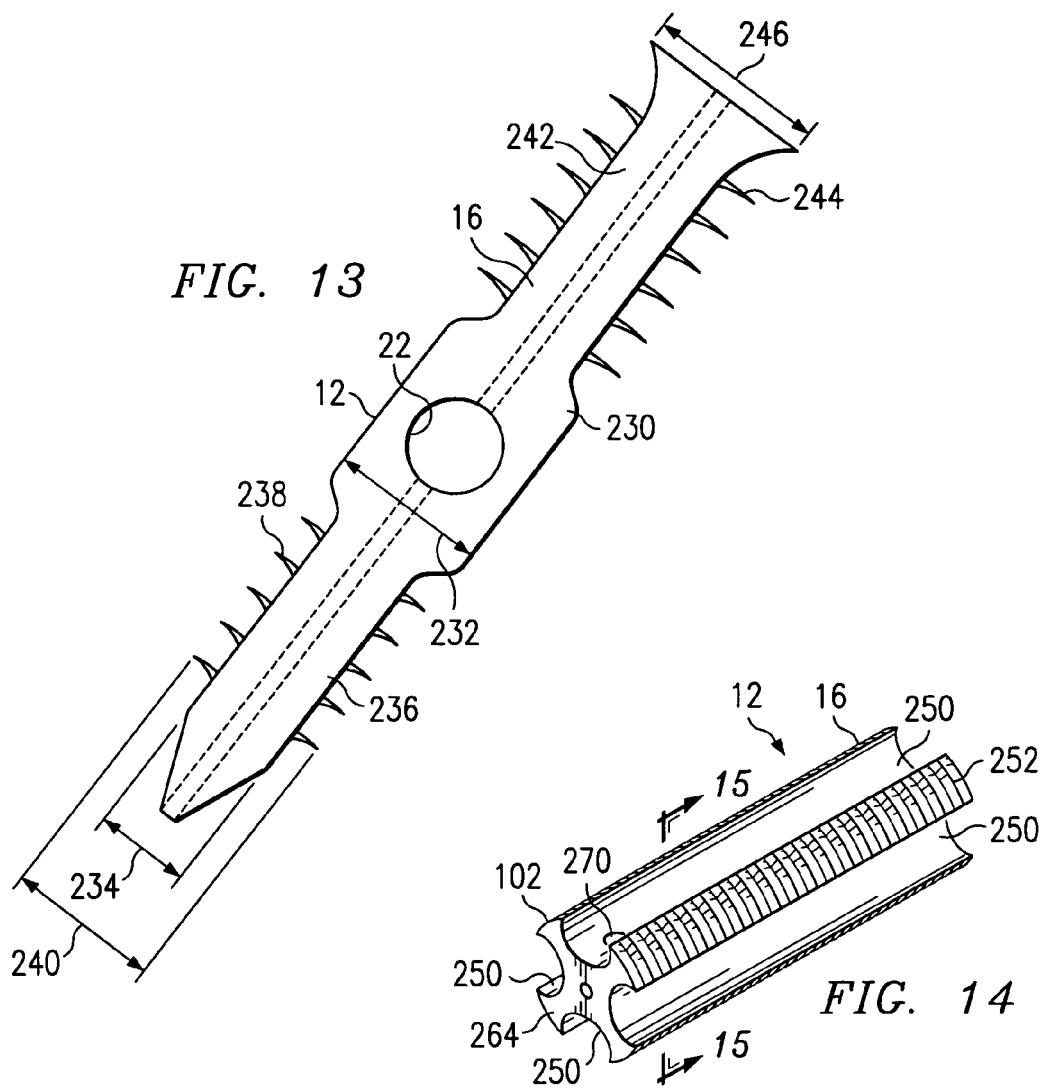
FIG. 13
FIG. 14
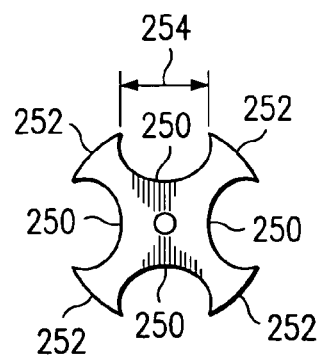
FIG. 15
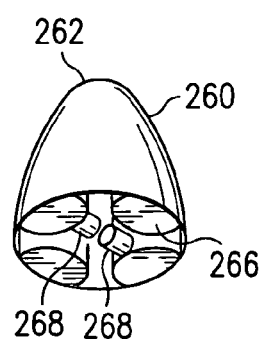
FIG. 16

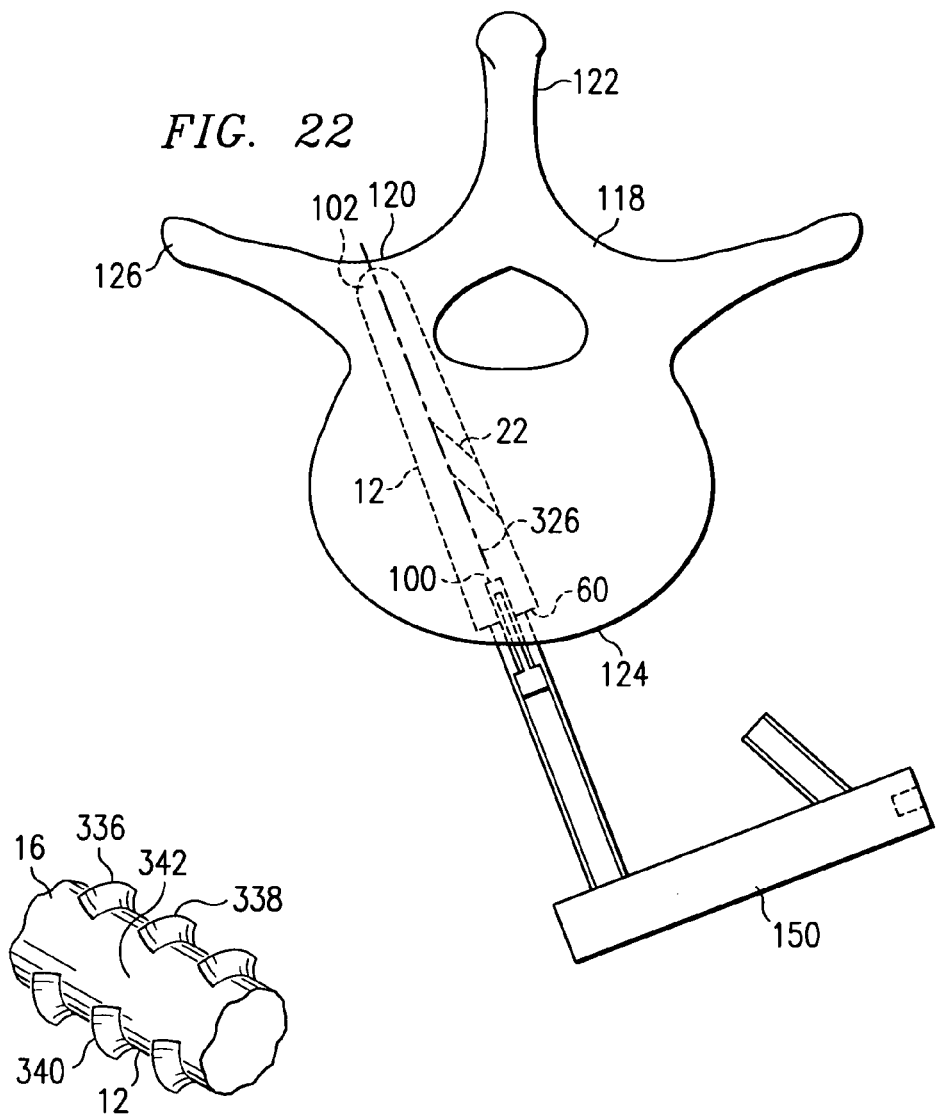
FIG. 22
FIG. 24
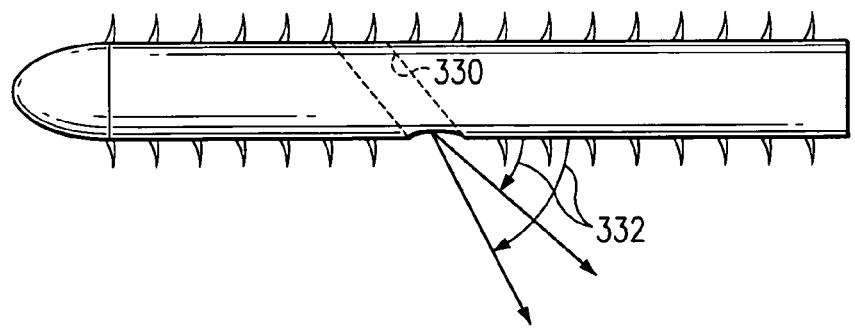
FIG. 23

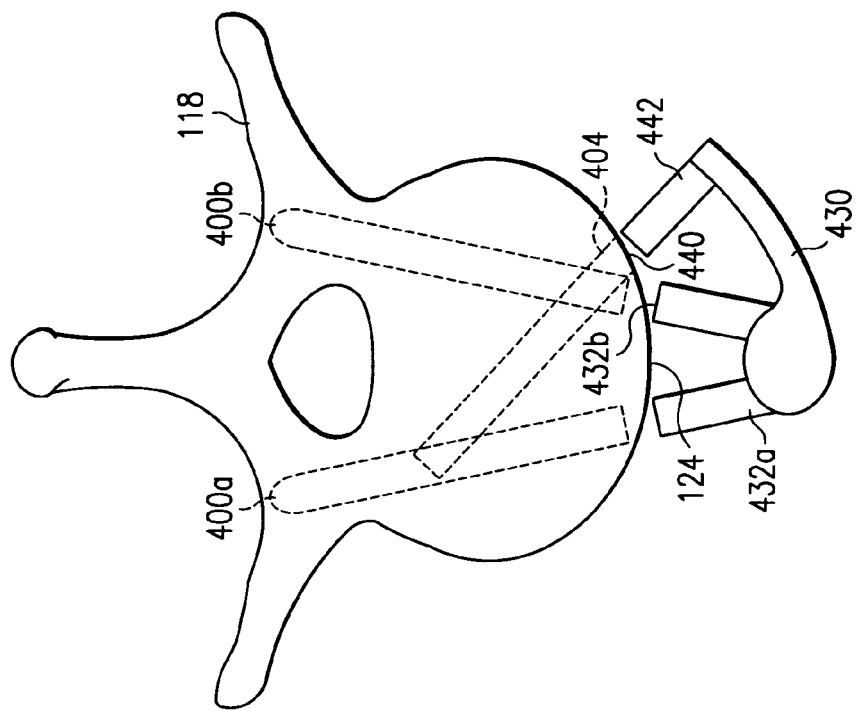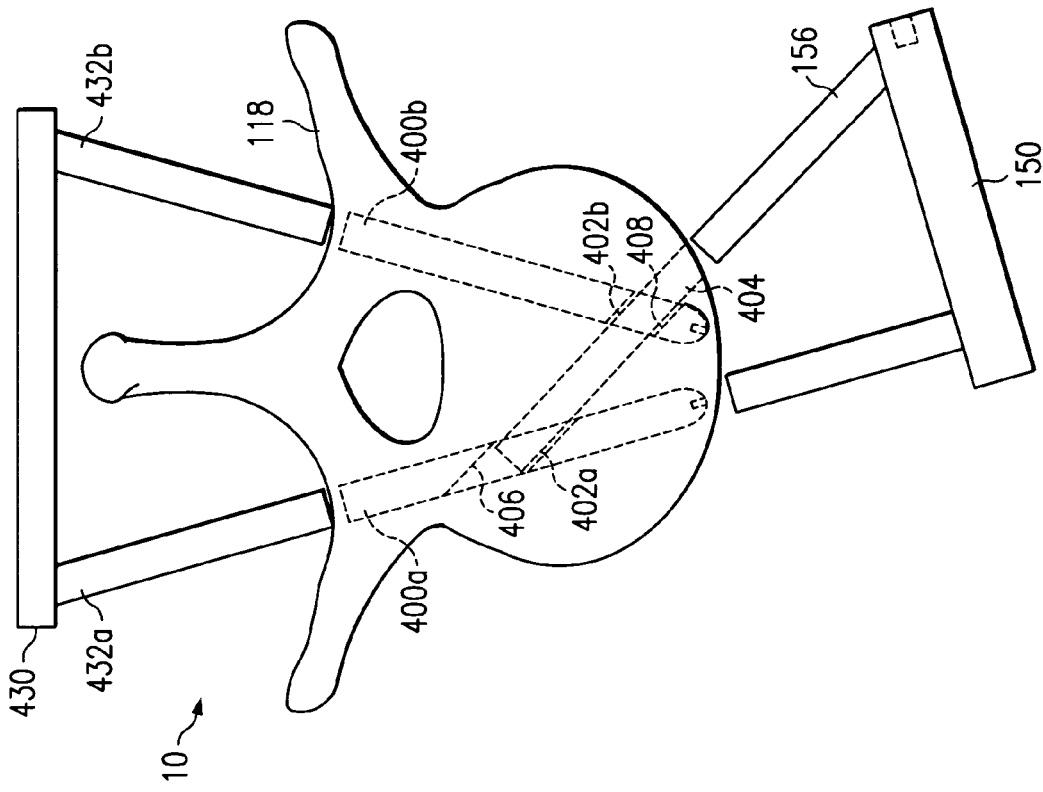

VERTEBRAL STABILIZATION ASSEMBLY AND METHOD

CROSS-REFERENCE TO RELATED APPLICATIONS

This patent application is a continuation of U.S. patent application Ser. No. 11/086,834, filed Mar. 22, 2005, which is a divisional of U.S. patent application Ser. No. 10/109,172, filed Mar. 28, 2002, now U.S. Pat. No. 6,899,714, issued May 31, 2005, which claims priority to U.S. Provisional Patent Application No. 60/327,118, filed Oct. 3, 2001, U.S. Provisional Patent Application No. 60/350,259, filed Nov. 2, 2001, U.S. Provisional Patent Application No. 60/331,857, filed Nov. 20, 2001, and U.S. Provisional Patent Application No. 60/353,691, filed Jan. 31, 2002, each of which is hereby incorporated by reference herein in its entirety.

TECHNICAL FIELD OF THE INVENTION

The present invention relates generally to a spinal stabilization and more specifically, but not by way of limitation, to a vertebral stabilization assembly and method for stabilizing vertebra.

BACKGROUND OF THE INVENTION

The human spine frequently requires surgery to repair deformities or injuries. Spinal problems may be caused by a trauma to the spine received during an accident, excessive strain or stress on the spine from physical activities, a sedentary lifestyle and poor posture that may place abnormal pressure on the spine, disease or a variety of other reasons. Spinal fusion is a common surgery intended to alleviate pain caused by these spinal deformities or injuries.

The spinal fusion procedure generally includes removing the disk, packing bone graft between the vertebrae and placing a spinal implant, such as screws attached to a plate, rod or cage, to fuse elements of the spine together. Once the disk is removed and the bone graft is placed between the vertebrae, the bone graft will fuse to the vertebrae over a period of several months following the surgery.

The purpose of the plate is to stabilize the vertebrae until the bone graft has become fused to the vertebrae. The plate is positioned to extend between at least two vertebrae. The plate is attached to screws anchored in each of the adjacent vertebrae, thus immobilizing the desired portion of the spine. The plate is anchored to the screws either on the front, anterior, or back, posterior, sides of the vertebrae.

The present invention is not intended to be limited to applications in a specific region of the spine, and may, in fact, be utilized equally well with the cervical, thoracic, lumbar and sacrum vertebrae of the spine. However, for purposes of explanation, the surgical procedure will be discussed in greater detail with respect only to the lumbar vertebrae region of the spine. Procedurally, anterior, or entry from the stomach region of the patient, lumbar vertebra surgery provides the surgeon with optimum access to the entire intervertebral disk. Posterior, or entry from the back of the patient, surgery is less preferred since access to the disk is restricted. Once the anterior lumbar discectomy, or removal of the lumbar disk, is completed, the bone graft is placed into the space between the vertebrae previously occupied by the disk.

The patient is then positioned for posterior fusion, or placement, of the plate. The stabilization is typically accomplished by placing a screw in each of the lumbar vertebra such the screw extends through a portion of the vertebra and into the body of the vertebra. Each screw extends posteriorly from the vertebra sufficient for attachment to the plate. The plate is then anchored to each of the screws to retain the adjacent lumbar vertebrae positioned a distance from each other. The plate and screws thereby stabilize the lumbar vertebrae and provide time for the vertebrae and bone graft to fuse into a solitary unit.

However, posterior fusion requires large posterior muscle dissection to safely implant the pedicle screws and provide for placement of the plate. Such major muscle damage presents a danger to the patient during surgery from infection and the extensive muscle damage. Also, additional time is required to perform both extensive anterior and posterior surgical portions. The added surgical time presents another risk to the patient.

Attempts to eliminate the negative aspects of posterior fusion include anterior placement of the plate and screws. Although anterior fusion avoids the problems associated with the larger posterior fusion, additional problems arise. In such systems, the anchoring screws are laterally placed on the anterior of the vertebra. Lateral placement requires a significantly more invasive procedure and much greater exposure. Also, screws anchored laterally through the anterior of the vertebra do not provide the stability of those extending posteriorly through the pedicle and into the vertebral body. Furthermore, anteriorly-anchored screws do not promote quick and uniform fusion of the bone graft to the vertebra since they do not have the stability of the pedicle fixation.

Thus a need exists for a vertebral stabilization assembly that obtains the benefits while overcoming the disadvantages of prior procedures and systems.

SUMMARY OF THE INVENTION

The present invention provides a vertebral stabilization assembly for stabilizing vertebra. The vertebral stabilization assembly includes a first and a second pedicle screw, a first and a second connecting screw and a connecting member. The first pedicle screw has a shaft provided with a threaded portion operable for threading engagement of the first pedicle screw with a first vertebra, the shaft also has an engaging portion. The first connecting screw has a first end adapted to be received by the engaging portion of the first pedicle screw.

The second pedicle screw has a shaft provided with a threaded portion operable for threading engagement of the pedicle screw with a second vertebra. The shaft of the second pedicle screw has an engaging portion. The second connecting screw has a first end adapted to be received by the engaging portion of the second pedicle screw. The connecting member has a first end and the second end. The first end of the connecting member connected to the first connecting screw positionable in the first vertebra. The second end of the connecting member connected to the second connecting screw positionable in the second vertebra for stabilization of the first vertebra and the second vertebra.

In one aspect, the connecting member may be a rod, bracket, plate or brace. In other aspects, the first and second connecting screws are each provided with an opening in a second end thereof and wherein the first end of the rod is positionable in the opening in the second end of the first connecting screw and wherein the second end of the rod is positionable in the opening in the second end of second connecting screw.

In one aspect, the present invention further comprises a first and second tensioning mechanism, the first tensioning mechanism tensioningly engaging the first end of the rod in the opening in the second end of the first connecting screw and the second tensioning mechanism tensioningly engaging the second end of the rod in the opening in the second end of the second connecting screw.

In other aspects, the first and second connecting screws are provided with coupling portions operable to couple the first and second connecting screws with the connecting member. In other aspects, the coupling portions of the first and second connecting screws are further defined as a threaded end of the first and second connecting screws.

In other aspects, the threaded end of the first and second connecting screws are connectable to the connecting member by bolts. While in other aspects, the connecting member connected to the first and second connecting screw is sized to retain the first vertebra disposed a distance from the second vertebra. The connecting member may be sized to retain the first vertebra disposed so as to prevent contact with the second vertebra.

In other aspects, the first and second pedicle screws are operable to engage a first and second lumbar vertebra, respectively.

In yet another aspect the vertebral stabilization assembly further includes a bore screw having a shaft sized similar in diameter to the shaft of the first and second pedicle screw. In one aspect, the diameter of the shaft of the bore screw is substantially similar to the diameter of the shaft of the pedicle screw, while in other aspects the diameter of the shaft of the bore screw is smaller, and in others larger, than the diameter of the shaft of the pedicle screw The bore screw is operative to bore an opening in the vertebra, from the posterior side of the vertebra.

The bore screw is useful to create a bore opening in the vertebra that is at a desirable angle in the vertebra. The bore screw may then be located from the anterior side and removed anteriorly according to one aspect or removed posteriorly according to another aspect of the present invention. Where the bore screw is removed anteriorly, the bore screw is provided with an engaging portion on a distal end of the bore screw for connection of the bore screw by a tool for removal from the vertebral anterior.

One advantage of utilizing the bore screw is that the angle of placement of the bore screw is known so that the proper pedicle screw may be selected based on the angle of penetration of the bore opening created in the vertebra by the bore screw, such as a pedicle screw having a engaging portion with the proper angle of connection for attachment of the connecting screw and a pedicle screw of appropriate length.

In another aspect, the vertebral stabilization assembly of the present invention further includes an indicator positionable posteriorly adjacent the bore opening created by bore screw. The indicator indicating the location of the bore opening from the anterior side of the vertebra. In one aspect, the indicator is an LED (light emitting diode) disposed on a rigid shaft extendable down the bore opening near the anterior side of the vertebra. In other aspects, the shaft may be substantially flexible for easy removal. In other aspects, the indicator is an LED or higher intensity light, such as a laser light, and is disposed posteriorly near the bore opening such that the light projects down the opening and is perceptible from the vertebral anterior.

In another aspect the present invention provides a pedicle screw for securing a connecting screw of a vertebral stabilization assembly. The pedicle screw includes a shaft, an engaging portion and coupling portion. The shaft has a threaded portion operable for threading engagement of the pedicle screw with a vertebra. The engaging portion is provided on the shaft and operable to receive a connecting screw of the vertebral stabilization assembly. The coupling portion is provided on the shaft and adapted to connect a guide member of the vertebral stabilization assembly. In one aspect of the pedicle screw of the present invention the shaft is cannulated. The cannulated portion of the shaft further defined as a passageway extending through the shaft from a first end of the shaft to a second end of the shaft.

In one aspect, the shaft is further defined as having a first end and a second end such that the threaded portion is adjacent the first end and the second end is operable to receive rotational engagement for rotating the pedicle screw. In yet another aspect, the engaging portion is further defined as an opening on the shaft operable to receive the connecting screw of the vertebral stabilization assembly.

In other aspects, the opening is further defined as extending through the shaft from a shaft first side to a shaft second side. In another aspect, the opening is coupleable with the connecting screw to provide stabilizing engagement of the connecting screw. While yet other aspects provide the opening is coupleable with the connecting screw to provide rigid engagement with the connecting screw.

In one aspect, the engaging portion is coupleable with the connecting screw to provide locking engagement with the connecting screw. In other aspects, the engaging portion is coupleable with the connecting screw to provide threaded engagement with the connecting screw. In yet other aspects, the coupling portion of the shaft is associated with the opening in the shaft such when the guide member is coupled to the coupling portion an alignment member of the guide member is aligned with the engaging portion in the shaft.

In one aspect, the coupling portion is further defined as an opening operable for threading engagement. In another aspect, the shaft is further defined as a substantially rigid shaft constructed from a material selected from the group consisting of steel, aluminum, metallic materials and polymeric materials. While in other aspects, the shaft is substantially cannulated such that a passageway extends through the shaft from a first end of the shaft to a second end of the shaft. In one aspect, the pedicle screw is operable to engage a lumbar vertebra. In another aspect, the pedicle screw is further operable to engage a thoracic vertebra.

In one aspect, the engaging portion on the shaft of the pedicle screw includes rotational portion for rotating the engaging portion for receiving the connecting screw at various angles relative to the shaft of the pedicle screw. In some aspects, the rotational portion includes a hinging member or a ratcheting member operative for rotation of the engaging portion. In other aspects, the engaging portion is disposed in an engaging opening in the shaft of the pedicle such that the engaging portion is rotatable within the engaging opening and, in some aspects, becomes fixed or locked when the connecting screw is received by the engaging portion.

In one aspect, the shaft of the pedicle screw is provided with at least one non-continuous thread extending circumferentially about the shaft such that at least one gap is disposed between a first portion of the non-continuous thread and a second portion of the non-continuous thread. The advantage of the disposition of the non-continuous thread is that when the nerve is aggravated by the placement of the pedicle screw, the pedicle screw may be rotated into a position such that the gap is adjacent the aggravated nerve instead of the thread to alleviate the aggravation which may be caused by the threaded portion of the shaft of the pedicle screw.

In another aspect, the shaft of the pedicle screw is provided with a first threaded portion and a reinforced portion. The reinforced portion of the shaft has a diameter that is greater than a diameter of the first threaded portion of the shaft. In one aspect, the reinforced portion of the shaft is substantially adjacent the engaging portion of the shaft for reinforcing the connection of the connecting screw to the pedicle screw via the engaging portion.

In another aspect the reinforced portion of the shaft is adjacent the first threaded portion and adjacent a second threaded portion, the diameter of the reinforced portion is greater than the diameter of the first threaded portion and about equal to a diameter measured from an outermost edge of a plurality of threads provided on the first threaded portion of the shaft. The diameter of the reinforced portion of the shaft is less than a diameter measured from an outermost edge of a plurality of threads provided on the second threaded portion of the shaft. The reinforced portion of the shaft is one advantage of the present aspect since the stability of the vertebral stabilization assembly is significantly enhanced by the additional structural support provided by the reinforced portion for connection of the connecting screw to the engaging portion of the pedicle screw adjacent the reinforced portion.

In yet another aspect, the shaft of the pedicle screw has at least a first groove extending a distance along the length of the shaft. In one aspect, a distal end of the shaft of the pedicle screw is substantially conical, while in other aspects, the distal end of the shaft is a substantially flat surface. In one aspect, where the distal end of the shaft is a substantially flat surface, the pedicle screw is provided with a cap which may have a conically shaped first end and a second end configured for mating connection near the distal end of the pedicle screw. In this aspect, the mating connection may be achieved by providing a recess in at least the first groove on the shaft and a notch on an inner surface of the cap such that the notch on the inner surface of the cap is tensioningly received by the recess in at least the first groove of the shaft.

In one aspect, the distal end of the pedicle screw is rectangularly configured for mating with a guide member for proper alignment of the engaging portion of the pedicle screw for connection of the connecting screw. In one aspect, only a portion of the shaft is provided with threads. In this aspect, the threads may be provided except on a portion of the shaft substantially adjacent the engaging portion. In other aspects, only a portion of the shaft above the engaging portion is provided with threads, while in other aspects only a portion of the shaft below the engaging portion is provided with threads.

In yet another aspect, the pedicle screw has a first end provided with a head operative for rotational engagement of the pedicle screw with the vertebra. A coupling portion is disposed adjacent the first end the pedicle screw and is further operative to engage a guide member of the vertebral stabilization assembly. In this aspect, the pedicle screw is provided for anterior placement such that a distal end of the pedicle screw which initially penetrates the vertebra from an anterior side of the vertebra engages and stabilizes from within the body portion of the vertebra near the pedicle of the vertebra. After placement of the pedicle screw, the head of the pedicle screw is disposed adjacent the anterior side of the vertebra for receiving a guide member.

One advantage of the pedicle screw for anterior placement and stabilization is that, when utilizing this aspect of the pedicle screw, placement of the vertebral stabilization assembly may be accomplished entirely from the patient's anterior eliminating the need to rotate the patient and further reducing the time needed for the surgical procedure. Utilizing the present aspect of the pedicle screw for anterior placement and stabilization provides numerous advantages even where portions of the medical procedure are accomplished from the patient's posterior. For example, in some aspects, it may be useful and necessary to rotate the patient and perform significant or peripheral procedures from the patient's posterior during certain portions of the vertebral stabilization procedure.

In yet other embodiments, the present invention provides a tool configured to connect to the distal end of the pedicle screw. In one aspect, the tool is provided with a first end having a handle adapted to be grasped by the hand of an individual and a second end provided with a connector to connect to the distal end of the pedicle screw to retain and stabilize the pedicle screw for placement and removal of the connecting screw. In one aspect the distal end of the pedicle screw is provided with an opening and the second end of the tool is provided with a connector configured to be received into the opening in the distal end of the pedicle screw for securing the pedicle screw.

In yet another aspect, the connecting screw is provide with at least a first groove on a shaft portion of the connecting screw for connection by a tool for retaining the connecting screw for placement and removal of the connecting screw. In one aspect, the connecting screw has an opening on one end of the connecting screw, and the tool is provided with a connector adapted to be received by the opening and configured to connect to the tool.

In yet another aspect, the present invention provides a guide member for placement of a screw of a vertebral stabilization assembly. The guide member including a coupling portion, and offset member, and an alignment member. The coupling portion is operable to couple with a coupling portion of a pedicle screw of the vertebral stabilization assembly. The offset member is connected to the coupling portion of the guide member. The offset member extending from the coupling portion relative to the connection of the coupling portion of the guide member to the coupling portion of the pedicle screw. The alignment member is connected to the offset member. The alignment member is operable for alignment of the connecting screw of the vertebral stabilization assembly with a portion of the pedicle screw of the vertebral stabilization assembly.

In one aspect, the coupling portion of the guide member is operable to couple with the coupling portion of the pedicle screw such that the offset member extends in a predetermined direction relative to the coupling of the coupling portion of the guide member to the coupling portion of the pedicle screw. While in other aspects, the offset member is further provided with a first end and a second end, and wherein the first end of the offset member is connected to the coupling portion and wherein the second end of the offset member is coupled to the alignment member.

In one aspect, the offset member is positionable relative to the coupling of the coupling portion with the end portion of the pedicle screw. While in other aspects, the offset member extends from the coupling portion adjacent a shaft portion of the pedicle screw.

In one aspect, the coupling portion of the guide member couples to the coupling portion of the pedicle screw such that the offset member positions the alignment member connected to the offset member substantially aligned adjacent a portion of the pedicle screw. In yet another aspect, the alignment member substantially aligns adjacent to the engaging portion of a shaft of the pedicle screw. While yet in other aspects, the alignment member substantially aligns adjacent an opening on the shaft of the pedicle screw. In yet another aspect, the alignment member provides alignment for threadingly taping the vertebra adjacent the opening in the pedicle screw.

In one aspect, the alignment member provides alignment for attachment of the connecting screw of the vertebral stabilization assembly to the pedicle screw. In other aspects, the alignment member is further defined as tubular member having a first end, a second end and a opening extending through the tubular member from the first end to the second end. While in yet other aspects, the opening extending through the tubular member is provided with a diameter sufficient to receive the connecting screw of the vertebral stabilization assembly through the opening in the tubular member for alignment with an engaging portion of a shaft of the pedicle screw of the vertebral stabilization assembly.

In another aspect, the present invention provides a vertebral stabilization assembly having dual pedicle screws including a first pedicle, a second pedicle screw and a connecting screw. The first pedicle screw has a shaft provided with a threaded portion operable for threading engagement of the first pedicle screw with a first vertebra. The shaft of the first pedicle screw has an engaging portion.

The second pedicle screw has a shaft provided with a threaded portion operable for threading engagement of the second pedicle screw with the first vertebra, the shaft of the second pedicle has an engaging portion. The connecting screw has a first end and a shaft, the first end of the connecting screw is adapted to be received by the engaging portion of the first pedicle screw. The shaft of the connecting screw is adapted for connection to the engaging portion of the second pedicle screw.

In yet another aspect, the present invention provides a method for stabilizing a lower vertebra and an upper vertebra from an anterior side of the vertebrae using a vertebral stabilization assembly. The method includes inserting a first pedicle screw into the lower vertebra through a pedicle and a vertebral body of the lower vertebra from a posterior side of the lower vertebra. The pedicle screw includes a shaft provided with a threaded portion operable to threadingly engage the lower vertebra. The shaft of the first pedicle screw has an engaging portion operable to receive a first connecting screw. The shaft of the first pedicle screw having a coupling portion operable to couple with a guide member of the vertebral stabilization assembly.

The method includes inserting a second pedicle screw into an upper vertebra through a pedicle and a vertebral body of the upper vertebra from a posterior side of the upper vertebra. The second pedicle screw includes a shaft provided with a threaded portion operable to threadingly engage the upper vertebra. The shaft of the second pedicle screw has an engaging portion operable to receive a second connecting screw. The shaft to the second pedicle screw has a coupling portion operable to couple with a guide member of the vertebral stabilization assembly. The method further includes locating the coupling portion of the shaft of the first pedicle screw from an anterior side of the lower vertebra.

The method includes coupling the guide member to the coupling portion of the shaft of the first pedicle screw from the anterior side of the lower vertebra. The method further provides for inserting a lower connecting screw through the anterior side of the lower vertebra using the guide member. The lower connecting screw includes a first end adapted to be received by the engaging portion of the first pedicle screw and a second end adapted to reside outside the lower vertebra on an anterior side of the lower vertebra.

The method includes locating the coupling portion of the shaft to the second pedicle screw from an anterior side of the upper vertebra. The method provides for coupling the guide member to the coupling portion of the shaft to the second pedicle screw from the anterior side of the upper vertebra. The method further includes inserting an upper connecting screw through the anterior side of the upper vertebra using the guide member. The upper connecting screw includes a first end adapted to be received by the engaging portion of the second pedicle screw and a second end adapted to reside outside the upper vertebra on the anterior side of the upper vertebra.

The method also provides for connecting the second end of the lower connecting screw of the lower vertebra to the second end of the upper connecting screw of the upper vertebra. In one aspect, the first and second pedicle screws are posteriorly placed on the right side of the lower and upper vertebra, respectively, and wherein the lower and upper vertebra are further defined as a lower and upper lumbar vertebra. In another aspect, the first and second pedicle screws are posteriorly placed on the right side of the lower and upper vertebra, respectively, and wherein the lower and upper vertebra are further defined as a lower and upper thoracic vertebra.

In one aspect, the present invention is directed to a method of anterior vertebral stabilization including placing from the patient's anterior the pedicle screw such that a portion of the pedicle screw is stabilized in a pedicle portion of the vertebra.

In one aspect, the first pedicle screw is further provided with a cannulated shaft having a passageway extending from a first end to a second end of the first pedicle screw and wherein locating the coupling portion of the shaft of the first pedicle screw from the anterior side of the lower vertebra further provides for extending a tool operable to drill through a portion of the lower vertebra through the passageway of the shaft of the first pedicle screw and drilling the portion of the lower vertebra such that the tool extends at least partially through the anterior side of the lower vertebra.

In one aspect, the second pedicle screw is further provided with a cannulated shaft having a passageway extending from a first end to a second end of the second pedicle screw and wherein locating the coupling portion of the shaft of the second pedicle screw from the anterior side of the upper vertebra further includes extending the tool operable to drill through a portion of the upper vertebra through the passageway of the shaft of the second pedicle screw and drilling the portion of the upper vertebra such that the tool extends at least partially through the anterior side of the upper vertebra.

In other aspects, coupling the guide member to the first and second pedicle screws further includes threadingly coupling the guide member to the coupling portion of the shaft of the first and second pedicle screws. In another aspect, coupling the guide member to the first and second pedicle screws further includes matingly coupling the guide member to the coupling portion of the shaft of the first and second pedicle screws.

In one aspect, inserting the lower connecting screw further includes positioning the lower connecting screw in alignment with the engaging portion of the first pedicle screw utilizing an alignment member of the guide member and threading the lower connecting screw through anterior side of the lower vertebra.

In one aspect, positioning the lower connecting screw in alignment with the engaging portion of the first pedicle screw further includes receiving the lower connecting screw by the alignment member of the guide member, the guide member adapted to position the alignment member connected thereto the guide member substantially aligned adjacent the engaging portion of the first pedicle screw.

In other aspects, inserting the upper connecting screw further includes positioning the upper connecting screw in alignment with the engaging portion of the second pedicle screw utilizing the alignment member of the guide member and threading the upper connecting screw through anterior side of the upper vertebra.

In one aspect, positioning the upper connecting screw in alignment with the engaging portion of the second pedicle screw further includes receiving the upper connecting screw by the alignment member of the guide member, the guide member adapted to position the alignment member connected thereto the guide member substantially aligned adjacent the engaging portion of the second pedicle screw.

In another aspect, connecting the upper connecting screw to the lower connecting screw further includes, providing a connecting member having a first end and a second end, connecting the second end of the lower connecting screw to the first end of the connecting member and connecting the second end of the upper connecting screw to the second end of the connecting member.

In yet another aspect, the connecting member is a plate and wherein the second end of the lower connecting screw receives the first end of the plate and wherein the second end of the upper connecting screw receives the second end of the plate.

In yet another aspect, the connecting member is a bracket and wherein the second end of the lower connecting screw receives the first end of the bracket and wherein the second end of the upper connecting screw receives the second end of the bracket. While in other aspects, the connecting member is a rod and wherein the second end of the lower connecting screw connects to the first end of the rod and wherein the second end of the upper connecting screw connects to the second end of the rod.

The pedicle screw of the present invention advantageously provides for posterior placement of the pedicle screw through a pedicle portion of the vertebra for secure attachment of the pedicle screw to the vertebra. The cannulated shaft of the pedicle screw is adapted to receive a drill bit there through such that the drill bit may be caused to drill through to the anterior side of the vertebra for easily locating the shaft of the pedicle screw. Another advantage of the present invention is that the pedicle screw is adapted for posterior placement through a pedicle portion of the vertebra for maximum stabilization. The connecting screw of the vertebral stabilization assembly is adapted to engage the engaging portion provided on the shaft of the pedicle screw to further promote a stable engagement of the vertebral stabilization assembly.

Yet another advantage of the present invention is that the engagement of the engaging portion of the shaft of the pedicle screw with the connecting screw prevents the pedicle screw or the connecting screw from moving or backing out of the vertebra since the connecting screw and pedicle screw are connected to one another.

Another advantage to the present invention is that the added stability of the pedicle screw posteriorly placed and connected to the connecting screw anteriorly insures for maximum stabilization and attachment of the connecting member and thus greater vertebral stabilization. Another advantage to the present invention is that the pedicle screw may be percutaneously placed by making only a small posterior incision and thus overcoming the disadvantages associated with posterior fusion requiring large posterior muscle dissection and the problems associated therewith. For this reason, the present invention is safer for the patient.

Anterior stabilization via connection to posteriorly placed pedicle screws has numerous advantages including significantly reducing the total time required for the surgical procedure. Avoidance of the radical muscle dissection required for posterior connection and stabilization is one factor in reducing the time to perform the surgery to about 2.5 hours versus the 5 to 7 hours such a procedures ordinarily requires. Thus, anterior stabilization via connection to posteriorly placed pedicle screws provides numerous advantages over prior vertebral stabilization systems and methods.

As well as being placed percutaneously, the pedicle screw may be positioned so that a head of the pedicle screw is substantially flush with the surface bone of the vertebra. Such placement further reduces interference with back muscles and associated problems and presents another advantage according to one aspect of the present invention.

Another advantage is that the present invention allows for the drill bit to be disposed within the cannulated portion of the shaft of the pedicle screw for only minor penetration of the surface of the anterior side of the vertebra to avoid the risk of damage to soft tissue adjacent the anterior of the vertebra.

Another advantage of the present invention is that the guide member allows for alignment of the connecting screw with the engaging portion of the pedicle screw without the necessity for time-consuming and inaccurate x-rays, MRI's, or other similar scanning or locating devices.

Another advantage of the present invention is that the method provides for placement of the vertebral stabilization assembly on an anterior side of the vertebrae eliminating many of the problems inherent in posterior fusion. Furthermore, elimination of the posterior fusion substantially reduces the amount of time required to perform the stabilization procedure according to the present invention.

Another advantage of the present invention is that by posterior placement of the pedicle screw in the pedicle portion of the vertebra and anterior stabilization via the connecting screw, the vertebral stabilization assembly of the present invention provides improved stabilization about a point central to the vertebral body versus about posterior or anterior edges of the vertebra. Thus, the present invention centrally distributes the stabilization pressures, tensions, weight, and stress as opposed to focusing the stabilization pressures about the outer edges of the vertebra. The central stabilization promotes improved stabilization of the vertebrae and improved fusion of the vertebrae.

In yet another aspect, the present invention provides a vertebral stabilization assembly having dual pedicle screws for placement in a first vertebra including a first pedicle screw, a second pedicle screw and a connecting screw. The first pedicle screw has a shaft provided with a threaded portion operable for threading engagement of the first pedicle screw with the first vertebra. The shaft of the first pedicle screw has an engaging portion.

The second pedicle screw has a shaft provided with a threaded portion operable for threading engagement of the second pedicle screw with the first vertebra, the shaft of the second pedicle screw has an engaging portion. The connecting screw has a first end and a shaft, the first end of the connecting screw is adapted to be received by the engaging portion of the first pedicle screw. The shaft of the connecting screw is adapted for connection to the engaging portion of the second pedicle screw.

In one aspect, the engaging portion of the second pedicle screw is defined as a threaded opening operable for the connecting screw to extend through and further operable to secure a portion of the shaft of the connecting screw.

In another aspect, a fixation tool is provided for placement of the first and second pedicle screws in the first vertebra so as to align the first and second pedicle screws for connection by the connecting screw. The fixation tool includes a first alignment member disposed adjacent a second alignment member, a third alignment member is offset relative to the first and second alignment members. The first and second alignment members of the fixation tool provide alignment for positioning the first and second pedicle screws in the vertebra. The third alignment member of the fixation tool aligns the connecting screw for coupling with the first and second pedicle screws.

Other objects, features, and advantages of the present invention will be apparent to those skilled in the art from the following detailed description when read in conjunction with the accompanying drawings and appended claims.

BRIEF DESCRIPTION OF THE DRAWINGS

For a more complete understanding of the present invention and the advantages thereof, reference is now made to the following brief description, taken in connection with the accompanying drawings and detailed description, wherein like reference numerals represent like parts, in which:

FIG. 13 is a perspective view illustrating yet another aspect of the pedicle screw provided with a shaft having a reinforced portion;

FIG. 14 is a perspective view of another aspect of the pedicle screw illustrating the shaft with at least a first groove and a flat surface on a distal end of the shaft constructed in accordance with the present invention;

FIG. 15 is a cross-sectional view of the shaft of the pedicle screw illustrated in FIG. 14 taken along line 15-15 thereof;

FIG. 16 is a perspective view of a cap according to one aspect of the present invention for attachment near the distal end of the pedicle screw;

FIG. 22 illustrates the guide member of the vertebral stabilization assembly attaching adjacent a head portion of the anteriorly placed pedicle screw according to one aspect of the present invention;

FIG. 23 is a top plan view of another aspect of the engaging portion of the pedicle screw of present invention for attachment to the connecting screw at various angles;

FIG. 24 is a perspective view of one aspect of the pedicle screw of the provided with non-continuous threads;

FIG. 25 is a top view of one aspect of the present invention illustrating placement of dual pedicle screws in the vertebra utilizing a fixation tool;

FIG. 26 is a top plan view of one aspect of dual pedicle screws invention illustrated anteriorly placed and connected to the connecting screw.

DETAILED DESCRIPTION OF THE INVENTION

It should be understood at the outset that although an exemplary implementation of the present invention is illustrated below, the present invention may be implemented using any number of techniques, whether currently known or in existence. The present invention should in no way be limited to the exemplary implementations, drawings, and techniques illustrated below, including the exemplary design and implementation illustrated and described herein.

Figure 1:
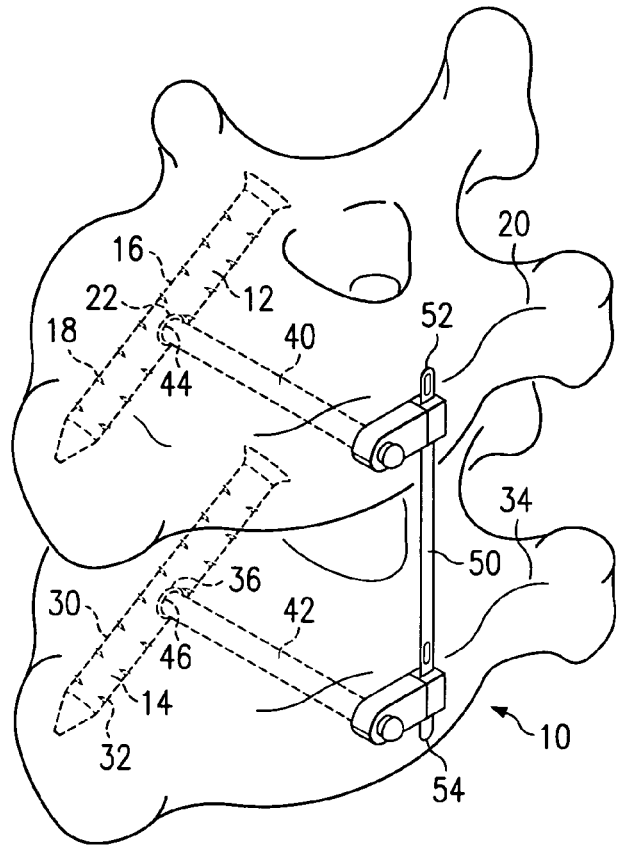
FIG. 1 is a perspective view of a vertebral stabilization assembly illustrated partially in phantom and shown stabilizing an upper and lower vertebra according to one aspect of the present invention.

FIG. 1 illustrates one aspect of the vertebral stabilization assembly 10 constructed in accordance with the present invention. The vertebral stabilization assembly 10 is an innovative device for stabilizing a plurality of vertebrae of the spine. The vertebral stabilization assembly 10 includes a first pedicle screw 12 and a second pedicle screw 14. The first pedicle screw includes a shaft 16 provided with a threaded portion 18. The threaded portion 18 of the shaft 16 is operable for threading engagement of the first pedicle screw 12 with a first vertebra 20. The shaft 16 of the pedicle screw 12 further includes an engaging portion 22.

The second pedicle screw 14 is substantially similar to the first pedicle screw 12 in that the second pedicle screw 14 includes a shaft 30 substantially similar to the shaft 16 of the first pedicle screw 12. The shaft 16 and 30 of the first and second pedicle screws 12 and 14, respectively, are substantially cylindrical members. The shaft 30 of the second pedicle screw 14 is similarly provided with a threaded portion 32 similar to the threaded portion 18 provided on the shaft 16 of the first pedicle screw 12. The threaded portion 32 of the shaft 30 is operable for threading engagement of the second pedicle screw 14 with a second vertebra 34. The shaft 30 of the first pedicle screw 14 is provided with an engaging portion 36.

The shafts 16 and 30 of the first and second pedicle screws 12 and 14 are of appropriate length to sufficiently anchor the first and second pedicle screws 12 and 14 in the first and second vertebra 20 and 34, respectively. The threaded portions 18 and 32 of the first and second pedicle screws 12 and 14 may be threads similar to those on ordinary screws and extending a distance from the shafts 16 and 30 sufficient to promote optimum anchoring of the first and second pedicle screws 12 and 14 within the first and second vertebra 20 and 34, respectively. The first and second pedicle screws 12 and 14 are constructed of a rigid material such as, but not limited to, steel, metal, or metal alloys, polymeric material, or a variety of other substantially rigid materials adapted to promote rigid engagement of the first and second pedicle screws 12 and 14 to the first and second vertebra 20 and 34, respectively.

The vertebral stabilization assembly 10 is further provided with a first connecting screw 40 and a second connecting screw 42. The first and second connecting screws 40 and 42 are substantially cylindrical members and may be constructed from materials similar to that of the first and second pedicle screws 12 and 14, such as, but not limited to, titanium, steel, metal or other metal alloys, substantially rigid polymeric material or a variety of other rigid metallic materials adapted and suitable for these purposes. The first connecting screw has a first end 44 adapted to be received by the engaging portion 22 on the shaft 16 of the first pedicle screw 12. The second connecting screw 42 has a first end 46 adapted to be received by the engaging portion 36 of the shaft 30 of the first pedicle screw 14.

The vertebral stabilization assembly 10 further includes a connecting member that has a first end 52 and a second end 54. The first end 52 of the connecting member 50 is connected to the first connecting screw 40 that is positionable in the first vertebra 20. The second end 54 of the connecting member 50 is connected to the second connecting screw 42 positionable in the second vertebra 34 for stabilization of the first vertebra 20 and the second vertebra 34. The connecting member 50 may be constructed from a variety of materials similar to that of the first and second pedicle screws 12 and 14 such as, but not limited to, titanium, steel, metal, or other metal alloys, rigid polymeric material, or other rigid materials suitable for stabilization of the first and second vertebra 20 and 34 by connection to the first and second connecting screws 40 and 42.

Figure 2:
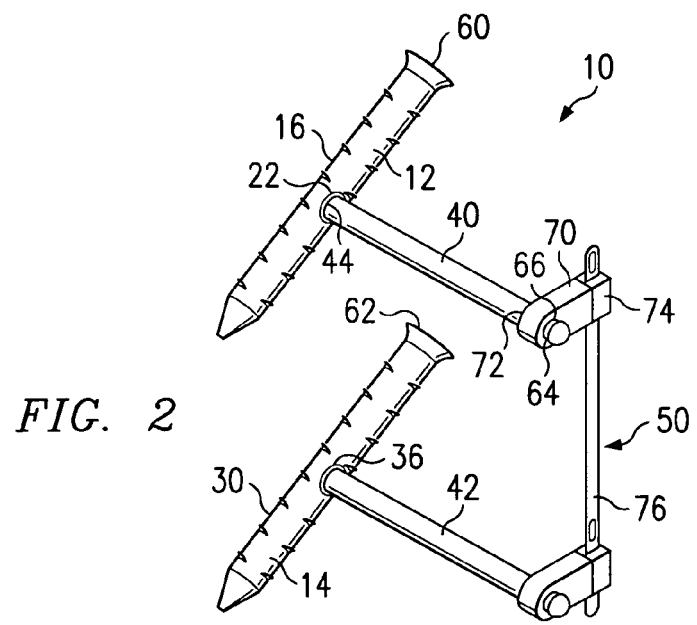
FIG. 2 is a perspective view of the vertebral stabilization assembly, as shown in FIG. 1, constructive in accordance with the present invention.

FIG. 2 illustrates the vertebral stabilization assembly 10, substantially as shown in FIG. 1, with the first and second vertebra 20 and 34 removed from the illustration for the purpose of further describing the present invention. It can be seen that the first and second pedicle screws 12 and 14 are provided with a head 60 and 62, respectively. The heads 60 and 62 of the first and second pedicle screws 12 and 14 may be configured to receive a tool, such as, but not limited to, a standard flat or a Phillips-head screw driver, Allen or other wrench connection, or a variety of male to female or female to male temporary interconnections for threadingly engaging the first and second pedicle screws 12 and 14 into the first and second vertebra 20 and 34.

In other embodiments (not shown) the heads 60 and 62 of the first and second pedicle screws 12 and 14 may be configured unlike the head of the standard screw and instead unitarily formed, for example, rectangularly from the shaft 16 and 30 for mating engagement with a unique tool adapted to receive the rectangularly-formed shaft.

It will be appreciated that a variety of constructions and configurations of the heads 60 and 62 of the first and second pedicle screws 12 and 14 will readily suggest themselves to one of ordinary skill in the art and may be provided in numerous configurations such that a tool may be attached temporarily to the heads 60 and 62 for imparting a rotation upon the first and second pedicle screws 12 and 14.

In the present illustration, the engaging portion 22 of the shaft 16 can be more easily seen as adapted to receive the first end 44 of the first connecting screw 40. The engaging portion 22 of the shaft 16 is a threaded opening formed in the shaft 16 of the first pedicle screw 12 and adapted to receive a threaded first end 44 of the first connecting screw 40. In this manner the first connecting screw 40 threadingly engages the engaging portion 22 to achieve a rigid locking connection between the first pedicle screw 12 and the first connecting screw 40.

In other embodiments (not shown) the engaging portion 22 may be a tension connection opening in the shaft 16 for receiving and engaging in a tensioning fashion the first end 44 of the first connecting screw 40. In yet other embodiments (not shown) the engaging portion 22 may be a locking assembly adapted to receive the first end 44 of the first connecting screw 40 and lock into place upon insertion. The locking engagement of the engaging portion 22 may be accomplished in a variety of manners including a keyed design of the engaging portion 22 such that when the first end 44 of the first connecting screw 40 is inserted into the engaging portion 22 it is locked into place upon rotation of the first connecting screw 40.

Yet in other embodiments (not shown), the engaging portion 22 may be a modification to the outer surface of the shaft 16 of the first pedicle screw 12 such that the first end 44 of the first connecting screw 40 may be adapted to receive the engaging portion 22 of the shaft 16 within an opening in the first end 44 of the first connecting screw 40. In this manner the locking or tensioning mechanism may be retained by the first end 44 of the first connecting screw 40 for engaging the first connecting screw 40 with the first pedicle screw 12.

A number of other connections including spring, ball, or other tensioning connections, as well as, threading, locking, and other mating connections for engaging the first end 44 of the first connecting screw 40 with the engaging portion 22 of the shaft 16 of the first pedicle screw 12 will readily suggest themselves to one of ordinary skill in the art and are within the spirit and scope of the present invention. It will be appreciated that the engaging portion 36 of the shaft 30 of the second pedicle screw 14 may be constructed substantially identical to the engaging portion 22 of the shaft 16 of the first pedicle screw 12. For purposes of brevity no further discussion of the engaging portion 36 is deemed necessary to enable one of ordinary skill in the art on the variety of means for engaging the first and second connecting screw 40 and 42 with the first and second pedicle screw 12 and 14 in light of the discussion regarding the engaging portion 22 of the first pedicle screw 12.

The first connecting screw 40 is constructed substantially similar to the second connecting screw 42 and for this reason, only the first connecting screw 40 will be discussed and described for purposes of brevity. The first connecting screw 40 is connected to the connecting member 50 near a second end 64 of the first connecting screw 40. The connection of the first connecting screw 40 to the connecting member 50 may be accomplished in a variety of manners such as, as shown in the present illustration, by providing a threaded portion on the second end 64 of the first connecting screw 40.

In this manner, a coupling 70 may be coupled to the second end 64 of the first connecting screw 40 and attached using a standard nut threadingly engaged with the threaded portion 66 of the second end 64 of the first connecting screw 40. The coupling portion 70 may be provided with an offset member 74 adapted to receive a rod 76. The offset member 74 thereby tensions the portion of the rod 76 extending through the offset member 74 for rigid engagement of the rod 76 to the coupling 70.

The tensioning engagement of the rod 76 by the offset member 74 may be accomplished by providing a screw (not shown), or other tension-imparting structure, threaded through the offset member 74 and into contact with the portion of the rod 76 extending through the offset member 74. The use of the coupling 70 and the rod 76 is a simple and useful design, according to one aspect, of the connecting member 50 for stabilization of the first and second vertebrae 20 and 34 via the first and second connecting screws 40 and 42.

It should be appreciated, however, that the connecting member 50 may be accomplished utilizing a variety of other structural connections to the first and second connecting screws 40 and 42. For example, in one embodiment (not shown), an opening may extend through the second end 64 of the first connecting screw 40. The opening of sufficient diameter to receive the rod 76 there through the opening in the second end 64 of the connecting screw 40. A tensioning connection, such as a screw or a nut may be utilized to tensionally engage the rod thereto the second end 64 of the first connecting screw 40. Other configurations of the coupling 70 may be utilized for these purposes and are within the spirit and scope of the present invention and will readily suggest themselves to one of ordinary skill in the art.

Figure 3:
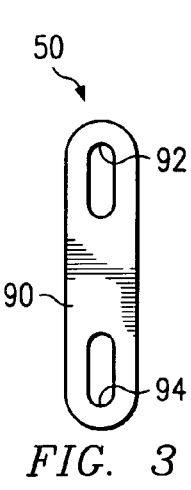
FIG. 3 is a side view of a connecting member constructed in accordance with one aspect of the present invention.

FIG. 3 illustrates a side view of another aspect of the connecting member 50 of the vertebral stabilization assembly 10 of the present invention. In this aspect the connecting member 50 is a bracket 90 having a first opening 92 and a second opening 94. The bracket 90, as with the various aspects of the connecting member 50, may be constructed from a variety of substantially rigid materials such as titanium, steel, metal or metal alloys, rigid polymeric material and other substantially rigid materials which may be utilized for these purposes.

The bracket 90 is a substantially flat plate provided with the first and second openings extending there through for receiving the first and second connecting screws 40 and 42. In this manner, the second end 64 of the first connecting screw 40 may be cause to extend through the first opening 92 of the bracket 90. The nut or other similar device 72 can then be threadingly engaged about the threaded portion 66 and caused to rigidly engage the bracket 90 to the second end 64 of the first connecting screw 40. Similarly, the second opening 94 may be adapted to receive the second connecting screw 42 for attachment thereto.

The symmetrical nature of the vertebral stabilization and assembly 10 lends itself to stabilization of a plurality of vertebrae. That is, the first and second pedicle screws 12 and 14 are substantially similar, as are the first and second connecting screws 40 and 42. Thus, while only a first and second pedicle screws 12 and 14 and a first and second connecting screws 40 and 42 are shown, the present invention contemplates stabilization of two or more vertebrae and is well suited for these purposes. In other embodiments (not shown) a third, fourth, or more pedicle screws may be utilized for engagement of a third, fourth, or more connecting screws for stabilization of a plurality of vertebrae. As such, the connecting member 50, or the bracket 90, shown in FIG. 3, will be provided having appropriate length or with the appropriate number of openings to receive each of the connecting screws for stabilizing the desired number of vertebrae.

One advantage of the vertebral stabilization assembly 10 of the present invention is that the connecting member fifty, whether utilizing the bracket 90 or the coupling 70 with the rod 76 (see FIG. 2) is adapted for connection on the anterior or front side of the vertebrae. The connecting member 50 according to the present invention has a low profile and thus minimizes the interference with soft tissue within the anterior of the patient.

Another advantage of the present invention is that the first pedicle screw 12 engaging the first connecting screw 40 provides for maximum stabilization in the vertebra 20. As such secure attachment to the vertebra 20 is optimized and greater stabilization can be accomplished by the innovations provided according to the present invention. Furthermore, the first pedicle screw 12 so connected to the first connecting screw 40 has the effect of inhibiting the first pedicle screw 12 from backing out of the vertebra 20, as well as preventing the first connecting screw 40 from backing out of the vertebra 20 as well.

Figure 3A:
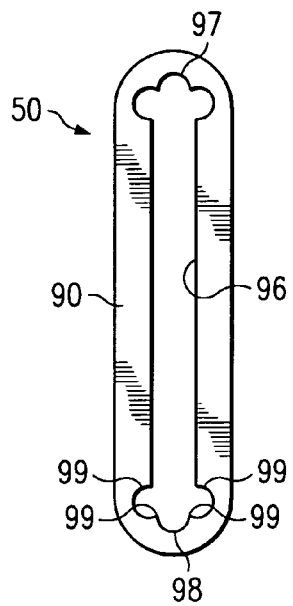
FIG. 3A is a side view of yet another aspect of the connecting member of the present invention.

FIG. 3A illustrates another aspect of the connecting member 50 that is similar to the bracket 90, illustrated in FIG. 3. In this aspect the bracket 90 is provided with a single opening 96 having a first end 97 and a second end 98 extending through the bracket 90. The opening 96 near the first and second ends 97 and 98 are provided with a plurality of notches 99 adapted for securely receiving a portion of a screw, such as the second end 64 of the first connecting screw 40.

The bracket 90 is useful where the first connecting screw 40 and the second connecting screw 42 are not substantially aligned vertically. Thus, the notches 99 are provided so that the first and second connecting screws 40 and 42 may be connected to the bracket 90 at various notches 99 on the first and second ends 97 and 98, respectively, of the bracket 90 while maintaining the bracket 90 disposed in a substantially vertical manner while the first and second connecting screws 40 and 42 may not be substantially vertical with respect to one another.

Figure 3B:
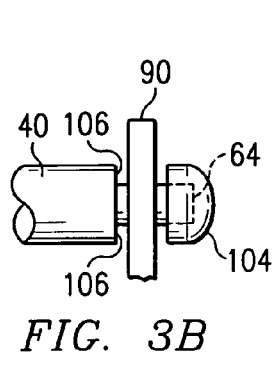
FIG. 3B is a side view of one aspect of a connecting screw shown with the connecting member attached to the connecting screw by a nut.

FIG. 3B illustrates another aspect of the first connecting screw 40 shown attached to the connecting member 50, such as the bracket 90, using a capped bolt 104. It can be seen that the second end 64 of the first connecting screw 40 is provided with a notch 106 such that the bracket 90 is flush against the notch 106 of the first connecting screw 40 for secure attachment thereto. A capped bolt 104 or other low-profile connectors may be utilized advantageously so as to minimize the interference and contact of the vertebral stabilization assembly 10 of the present invention with any of the soft tissue of the patient.

Figure 4:
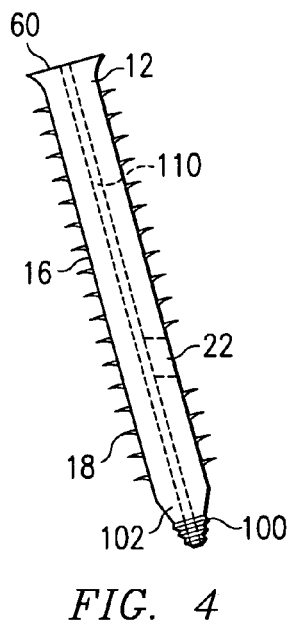
FIG. 4 is a side elevational view of a pedicle screw according to one aspect of the present invention.

FIG. 4 illustrates another aspect of the present invention of the pedicle screw, such as the pedicle screw 12, for securing a connecting screw, such as the first connecting screw 40, of the vertebral stabilization assembly 10 of the present invention. In this aspect the pedicle screw 12, as well as having the shaft 16 having the threaded portion 18 and the engaging portion 22, as previously discussed, further includes a coupling portion 100 provided on the shaft 16.

The coupling portion 100 is adapted to connect a guide member (which will be discussed in greater detail with reference to FIG. 6) of the vertebral stabilization assembly. In one aspect the coupling portion 100 may be a threaded portion on the outer surface of the shaft 16 near the distal end 102 of the shaft 16. The guide member may be threadingly connected to the coupling portion 100 about the distal end 102 of the shaft 16. In other embodiments, however, the coupling portion may be an opening provided in the distal end 102 of the shaft 16 such that a portion of the guide member may be threadingly received within the opening in the distal end 102 of the shaft 16 for threading engagement therewith the coupling portion 100.

As previously mentioned, the engaging portion 22 of shaft 16 is operable to receive the first connecting screw 40. The engaging portion 22 in one embodiment may be provided as an opening on the shaft 16 extending completely through the shaft 16. The purpose of the engaging portion 22, as previously discussed, is to provide stabilizing engagement of the first connecting screw 40 with the first pedicle screw 12. As previously discussed, this rigid engagement may be provided in a variety of manners, such as, but not limited to, a locking engagement, a threading engagement, a tensioning or other rigid coupling connection of the first connecting screw 40 with the first pedicle screw 12 about the engaging portion 22.

Figure 5:
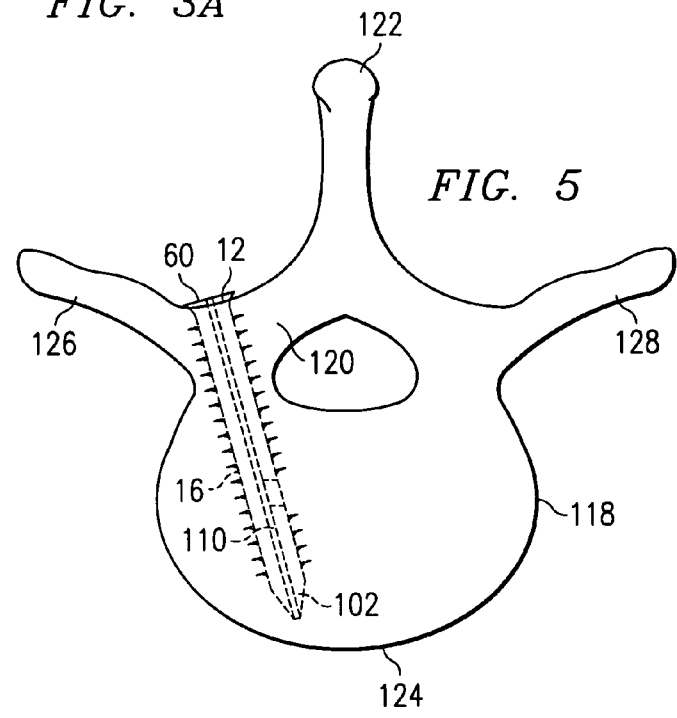
FIG. 5 is a top plan view of the pedicle screw, illustrated in FIG. 4, shown posteriorly positioned in a lumbar vertebra in accordance with the present invention.

Referring also to FIG. 5 a top view of a vertebra 118, such as a lumbar vertebra, shown with the first pedicle screw 12 set therein. One advantage of the present invention is that the first pedicle screw 12 may be placed through a pedicle 120 on a posterior side 122 of the vertebra 118.

Posterior placement through the pedicle 120 of the vertebra 118 provides optimum stability and anchoring of the first pedicle screw 12 by threading engagement through the most rigid portions of the vertebra 118. Significant problems arise when the first pedicle screw 12 is not well anchored within the vertebra 118 and alternate placement is then required. Furthermore, stabile anchoring is critical to reduce the likelihood that the first pedicle screw 12 will back out, or come backwards out of its placement, of the vertebra 118. The illustrated placement of first pedicle screw 12 advantageously overcomes the disadvantages associated with unstable attachment common with anterior vertebral stabilization systems.

As previously mentioned, the connecting member 50 is positionable on the anterior side 124 of the vertebra 118. Thus, the vertebral stabilization assembly 10 of the present invention achieves the advantages of anterior vertebral stabilization, since the connecting member is positioned on the anterior side 124 of the vertebra 118, while simultaneously achieving the stability associated with posterior procedures.

The first pedicle screw 12 may be placed in the vertebra 118, substantially as shown, percutaneously or through the skin requiring only a small incision, and avoiding the disadvantages associated with large, invasive posterior procedures which require significant interference and dissection of adjacent muscles.

In yet another aspect of the present invention the pedicle screw 12 may be provided with a cannulated shaft 16 such that a passageway 110 extends through the shaft 16 from the head 60 to the distal end 102 thereof the shaft 16. By utilizing the passageway 110 extending through the shaft 16 of the first pedicle screw 12, a tool (not shown) such as a tap or drill bit may be placed through this cannulated portion of the shaft 16 such that the tool or drill bit enters near the head 60 of the first pedicle screw 12. The tool is then extended through the passageway 110 towards the distal end 102.

The tool may then be utilized to drill through to the anterior side 124 of the vertebra 118 for location of the distal end 102 of the pedicle screw 12 from the anterior side 124 of the vertebra 118. Since only a small distance must be drilled, there is minimal risk to soft tissue or blood vessels. Furthermore, once the tool penetrates the anterior side 124 of the vertebra 118, the surgeon should be able to sense the reduced resistance and friction on the tool. Furthermore, the tool may be provided with stops or a drill bit may be cannulated to prevent extension of the drill beyond the anterior side 124 of the vertebra 118.

In the present embodiment right side 126 placement of the first pedicle screw 12 is preferable to avoid soft tissue injuries to the patient's anterior caused by penetration of the drill bit through the anterior side 124 of the vertebra 118 via the passageway 110 of the first pedicle screw 12. Anatomically, fragile soft tissue and blood vessels are positioned adjacent the right side 126 on the anterior side 124 of the vertebra 118. By using any number of surgical retraction techniques, these blood vessels may be held toward the right side 126 of the anterior side 124 of the vertebra 118. As such, the right side 126 placement of the first pedicle screw 12 represents the most efficient, as well as safest, placement for utilizing the first pedicle screw 12 in accordance with the present invention. In some instances, however, left side 128 placement of the first pedicle screw 12 in the vertebra 118 will be necessary. Left side 128 placement of the first pedicle screw 12 will be discussed in greater detail with reference to FIG. 8.

Figure 6:
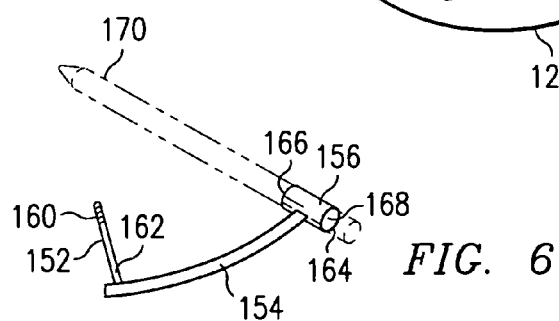
FIG. 6 is a perspective view of a guide member according to one aspect of the present invention for aligning a connecting screw shown in phantom.

FIG. 6 illustrates yet another aspect of the present invention of a guide member 150. The guide member 150 includes a coupling portion 152 an offset member 154 and an alignment member 156. The coupling portion 152 is operable to couple with the coupling portion 100 of the first pedicle screw 12 (see FIG. 4). The offset member 154 is connected to the coupling portion 152. The offset member 154 extends from the coupling portion 152 relative to the connection of the coupling portion 152 to the coupling portion 100 of the first pedicle screw 12. The alignment member 156 is connected to the offset member 154. The alignment member 156 is operable for alignment of the connecting screw, such as the first connecting screw 40, with a portion of the first pedicle screw 12, such as the engaging portion 22.

The guide member 150 may be constructed from a variety of materials such as, but not limited to, titanium, steel, metal or other metal alloys, a substantially rigid polymeric material, aluminum or other substantially rigid materials sufficient for these purposes. The coupling portion 152 is provided with a first end 160 and a second end 162. The first end 160 of the coupling portion 152 may be threaded for threading engagement to the coupling portion 100 of the first pedicle screw 12.

It should be appreciated, however, that a number of connecting methods may be utilized to accomplish the connection of the first end 160 of the coupling portion 152 to the coupling portion 100 of the first pedicle screw 12. For example, the first end 160 may be shaped so as to be substantially rectangular or other geometric shape about a portion of the first end 160 such that a similarly geometrically configured opening in the coupling portion 100 in the distal end 102 of the first pedicle screw 12 is adapted to receive the first end 160 of the coupling portion 152. Other locking or tensioning engagements of the first end 160 of the coupling portion 152 to the coupling portion 100 of the first pedicle screw 12, as well as a variety of other methods for achieving this attachment, will readily suggest themselves to one of ordinary skill in the art and are within the spirit and scope of the present invention.

The second end 162 of the coupling portion 152 is attached to the offset member 154. The attachment of the coupling portion 152 to the offset member 154 may be of a connecting, such as threading or tensioning or locking connection, or may be accomplished by a welded or bonded connection of the second end 162 of the coupling portion 152 to the offset member 154. Although welding or bonding engagements of various components of the vertebral stabilization assembly 10 of the present invention are preferable, it should be appreciated that bonding or other gluing or tacking materials may be used for this connection and satisfactory for these purposes.

The offset member 154 is shown as a substantially arcuate member extending from the second end 162 of the coupling portion 152 to the alignment member 156. However, in other embodiments, one of which is described hereinafter, the alignment member 156 may be comprised of a number of foldable or extendable or hinging segments to promote use within the confinements of the patient's anterior. While the offset member 154 is shown as a substantially rigid arcuate member, a number of other configurations of the offset member 154, such as a substantially straight member, or a stair-stepped member, as well as the offset member 154 being comprised of several connectable or extendable members are contemplated according to other aspects (not shown) of the present invention.

A number of configurations of the offset member 154, such as formation of a portion of the offset member 154 unitarily with the coupling portion 152 and formation of a remaining portion of the offset member 154 unitarily formed with the alignment member 156 may also be utilized for these purposes. Although the offset member 154 is shown in the preferred aspect, a variety of configurations of the offset member 154 will readily suggest themselves to one of ordinary skill in the art for positioning the alignment member 156 relative to a portion of the first pedicle screw 12 when the coupling portion 152 of the guide member 150 is connected to the coupling portion 100 of the first pedicle screw 12 and are within the spirit and scope of the present invention and will not be discussed in further detail for the purposes of brevity.

The alignment member 156 is rigidly connected to the offset member 154 by welding or bonding or other similar means. However, attachment of the alignment member 156 to the offset member 154 may be accomplished by a threading, locking or tensioning engagement and is satisfactory for these purposes. The alignment member 156 is a substantially tubular member having a first end 164 and a second end 166 and an opening 168 extending through from the first end 164 to the second end 166.

The alignment member 156 is provided such that the opening 168 is of a sufficient diameter to receive a drilling device 170, shown in phantom, through the opening 168 for alignment with the engaging portion 22 on the shaft 16 of the first pedicle screw 12. The drilling device 170 may be the a bit of a drill or other devices operative to drill an opening into vertebral bone. Thus, the alignment member 156 receives the drilling device 170 that drills an opening properly aligned for attachment of the first connecting screw 40 to the first pedicle screw 12. Thus, the guide member 150 is advantageously provided for creating an opening aligned with the engaging portion 22 of the first pedicle screw 12.

It should be appreciated that while the alignment member 156 of the present aspect is illustrated as a substantially tubular member having an opening 168, other embodiments the alignment member 156 may not be a completely tubular, and instead, be provided as a guide or positioning member for alignment of the first connecting screw 40 with the engaging portion 22 of the first pedicle screw 12.

Numerous configurations for aligning the first connecting screw 40 with the engaging portion 22 of the first pedicle screw 12 may be utilized for these purposes and will readily suggest themselves to one of ordinary skill in the art and are within the spirit and scope of the present invention and will not be discussed further for purposes of brevity.

Figure 7:
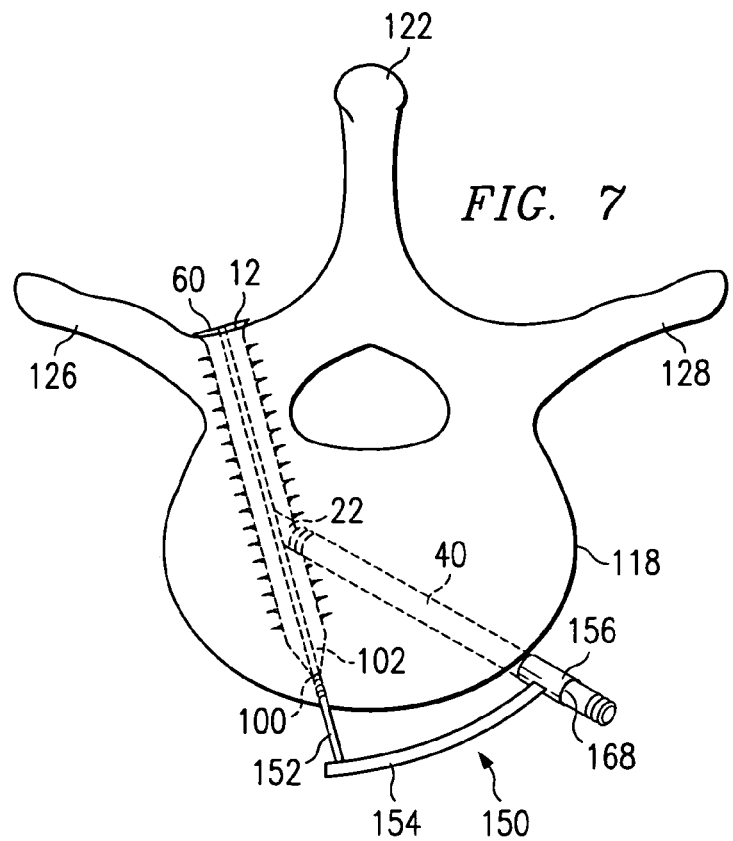
FIG. 7 illustrates alignment of the connecting screw utilizing the guide member for attachment of the connecting screw to the pedicle screw positioned within the lumbar vertebra, as shown in FIG. 5, according to one aspect of the present invention.

FIG. 7 illustrates a top view of the vertebra 118 shown with the first pedicle screw 12 positioned therein with the guide member 150 shown attached to the first pedicle screw 12. In this view, it can be seen that the guide member 150 is a useful tool for placement of the first connecting screw 40 for attachment to the engaging portion 22 of the first pedicle screw 12. It will be appreciated that, procedurally, the first pedicle screw 12 has been percutaneously placed through the posterior side 122 of the vertebra 118. Thereafter the tool, such as the drill, as previously discussed, is caused to drill through the anterior side 124 of the vertebra 118 thus locating the position of the coupling portion 100 on the distal end 102 of the first pedicle screw 12.

At this point, the guide member 150 may be positioned such that the coupling portion 152 extends through the drilled opening on the anterior side 124 of the vertebra 118. The coupling portion 152 of the guide member 150 is then connected to the coupling portion 100 of the first pedicle screw 12. An innovative aspect of the pedicle screw 12 is that the coupling portion 100 on the distal end 102 of the first pedicle screw 12 is associated with the engaging portion 22 on the shaft 16 of the first pedicle screw 12. The association of the coupling portion 100 and engaging portion 22 of the first pedicle screw 12 is a significant advantage of the first pedicle screw 12 according to the present invention. That is, this association allows for the guide member 150 to be configured relative to this association. Thus, the coupling portion 152 of the guide member 150, when coupled to the first pedicle screw 12, aligns the alignment member 156 with the engaging portion 22 on the shaft 16 of the first pedicle screw 12. Utilizing the guide member 150, several methods exist for aligning and securing the first connecting screw 40 to the first pedicle screw 12. It may be preferable to utilize the drilling device 170 to create an opening in the anterior side 124 of the vertebra 118. Thereafter, the guide member 150 may be removed and the first connecting screw 40 disposed through the opening drilled in the vertebra 118 and connected to the first pedicle screw 12.

In some instances, it may be beneficial for the alignment member 156 to be adapted to receive the first connecting screw 40 positioned to extend through the opening 168 of the alignment member 156. The first connecting screw 40 may then be drilled or threaded directly into the left side 128 of the anterior side 124 of the vertebra 118. Whether an opening is first drilled or the first connecting screw 40 is directly drilled into the vertebra 118, the unique configuration of the guide member 150 relative to the first pedicle screw 12 insures that the first connecting screw 40 will be properly aligned so as to locate the engaging portion 22 of the first pedicle screw 12 for engaging attachment thereto.

Thus, another advantage of the guide member 150 of the present invention is that the coupling portion 152 of the guide member 150 is operable to couple with the coupling portion 100 of the first pedicle screw 12 such that the offset member 154 extends in a predetermined direction relative to the coupling of the coupling portion 152 of the guide member 150 to the coupling portion 100 of the first pedicle screw 12. The offset member 154 of the guide member 150 is positionable relative to the coupling of the coupling portion 152 of the guide member 150 with the coupling portion 100 of the first pedicle screw 12.

It will be appreciated that the connection of the coupling portion 152 of the guide member 150 to the coupling portion 100 of the first pedicle screw 12 must be a locking or fitted type connection such that the offset member 154 properly extends in the proper direction to position the alignment member 156 for alignment with the engaging portion 22 of the first pedicle screw 12. Achieving the accuracy necessary to locate the engaging portion 22 of the first pedicle screw 12, which will not be visible since the first pedicle screw 12 will be embedded within the vertebra 118, is preferably accomplished through the accurate coupling connection of the coupling portion 152 of the guide member 150 to the coupling portion 100 of the first pedicle screw 12.

It should be understood, however, that a number of other methods of locating the engaging portion 22 of the first pedicle screw 12 for alignment with the first connecting screw 40 may be utilized. For example, providing indicia or markings on the head 60 of the first pedicle screw 12 indicating the relative position of the engaging portion 22 of the first pedicle screw 12. The coupling portion 152 may further include an extension (not shown) extendable through the passageway 110 of the shaft 16 of the first pedicle screw 12. The extension of the coupling portion 152 of the guide member 150 similarly provided with indicia, markings, or an alignment with the indicia provided on the head 60 of the first pedicle screw 12. In this manner, when the indicia are aligned, so is the alignment member 156 aligned with the engaging portion 22 on the first pedicle screw 12.

A variety of other methods for obtaining this positioning and alignment for connecting the first connecting screw 40 to the first pedicle screw 12 will readily suggest themselves to one of ordinary skill in the art and are within the spirit and scope of the present invention and will not be discussed for purposes of brevity.

Figure 8:
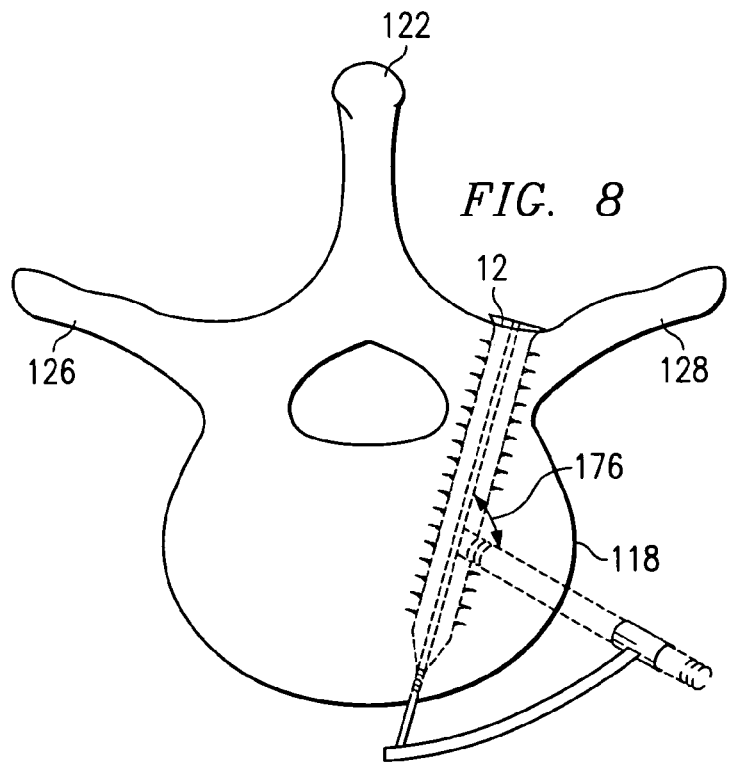
FIG. 8 illustrates a left side posterior positioning of the pedicle screw and alignment of the connecting screw utilizing the guide member according to yet another aspect of the present invention.

FIG. 8 illustrates an alternative left side 128 placement of the first pedicle screw 12 in the vertebra 118. Procedurally, numerous methods may be utilized to determine whether the first pedicle screw 12 is satisfactorily stabilized within the vertebra 118, including electrical stimulation to test for a desired threshold. In certain circumstances, such as when the right side 126 placement of the first pedicle screw 12 is ineffective to achieve the desired or required stability, left side 128 placement of the first pedicle screw 12 may be necessary. In this instance, the present invention may be utilized in substantially the same manner for left side 128 placement.

The significant difference between the first pedicle screw 12 utilized for right side 126 placement, as opposed to left side 128 placement, is an angle 176 of the engaging portion 22 of the first pedicle screw 12 relative to an axis extending centrally through the shaft 16, such as the passageway 110 of the first pedicle screw 12. It can be seen that the angle 176 of the engaging portion 22 of the first pedicle screw 12 necessary for placement of the first connecting screw 40 about the left side 128 of the anterior side 124 of the vertebra 118 varies considerably depending upon whether the first pedicle screw 12 is connected from the left side 128 or the right side 126 of the vertebra 118. For this reason, a unique first pedicle screw 12 and guide member 150 will be constructed for the left side 128 versus right side 126 placement, such that the guide member 150, when connected to the first pedicle screw 12, properly aligns the first connecting screw 40 based upon which vertebral placement, and corresponding first pedicle screw 12 is utilized.

Figure 9:
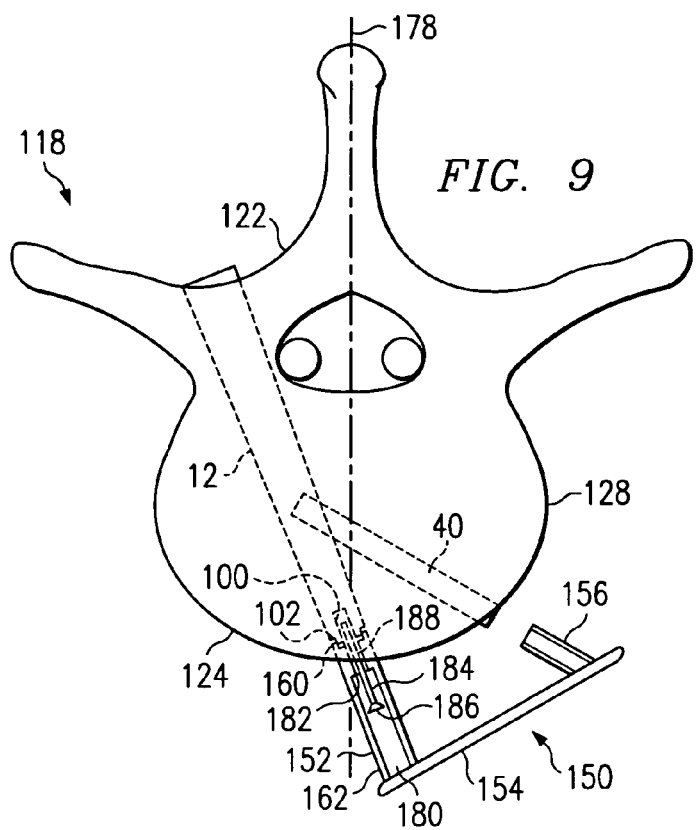
FIG. 9 is a top plan view of other aspects of the guide member and the pedicle screw shown connected in accordance with yet another aspect of the present invention.

FIG. 9 illustrates another aspect of the first pedicle screw 12 as well as another aspect of the guide member 150. The vertebra 118 is shown having a midline 178 extending from the anterior side 124 to the posterior side 122 of the vertebra 118. The coupling portion 152 of the guide member 150 is shown connected to the first pedicle screw 12 on the left side 128 of the vertebra 118 adjacent the midline 178. As previously discussed, placement of the first pedicle screw 12 on the left 128 anterior side 124 of the vertebra 118 may be preferable.

In this aspect the guide member 150 is shown having a substantially non-arcuate offset member 154 such that the alignment member 156 extends angularly therefrom the offset member 154. The coupling portion 152 is shown as a substantially tubular member having a channel 180 extending through the coupling portion 152. The coupling portion 152 is provided with a recess 182 extending into the channel 180 near the first end 160 of the coupling portion 152. Furthermore, in this aspect, the first end 160 of the coupling portion 152 is adapted to matingly receive the first pedicle screw 12 near the distal end 102 thereof. As previously discussed, the first pedicle screw 12 is provided with a coupling portion 100 provided, in this aspect, as an opening in the distal end 102 of the first pedicle screw 12.

A locking screw 184 may be extended through the channel 180 from the second end 162 toward the first end 160 of the coupling portion 152. The locking screw 184 is provided with a head 186 having a larger diameter than that of a shaft 188 portion of the locking screw 184. The first end 160 of the coupling portion 152 is matingly connectable to the distal end 102 of the first pedicle screw 12. The locking screw 184 is positioned through the channel 180 until the shaft 188 portion of the locking screw 184 couples with the coupling portion 100 of the first pedicle screw 12.

A tool (not shown) having any standard screw driver or hex, octagonal-type or other connection, for example, may be extended down the channel 180 and used to connect the locking screw 184 to the coupling portion 100 of the first pedicle screw 12. The locking screw 184 may be threadingly screwed into engagement with the first pedicle screw 12 or connected in other manners which are well known and will readily suggest themselves to one of ordinary skill in the art.

In this manner, the head 186 of the locking screw 184 engages the recess 182 within the channel 180 of the coupling portion 152 thereby engaging the coupling portion 152 to the first pedicle screw 12. It will be appreciated that the locking screw 184, the coupling portion 152 and the guide member 150 may be provided with indicia or markings to indicate locking engagement and alignment with both the first pedicle screw 12 and the vertebra 118 since it is critical that the locking screw 184 couple the coupling portion 152 to the first pedicle screw 12 at a particular position relative to the vertebra 118. The indicia or markings may include cross-hair lines, a single line or mark, an arrow, or other markings indicating a rotational position desired for achieving this connection and location.

Such accurate positioning may be accomplished based on the threads of the shaft 188 of the locking screw 184 corresponding to threaded openings within the coupling portion 100 of the first pedicle screw 12. A variety of different structural attachments for obtaining this locking connection for alignment of the guide member 150 with the first pedicle screw 12 such that the alignment member 156 is substantially aligned with the engaging portion 22 on the shaft 16 of the first pedicle screw 12 may be utilized and are within the spirit and scope of the present invention and will readily suggest themselves to one of ordinary skill in the art.

Figure 10:
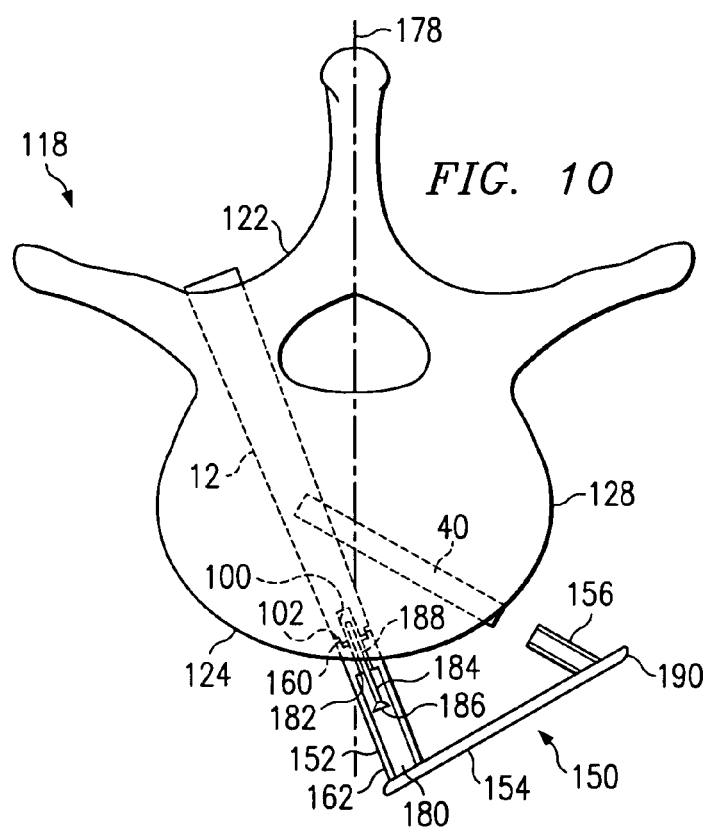
FIG. 10 illustrates alignment of the connecting screw utilizing the guide member, as shown in FIG. 9, for attachment of the connecting screw to the pedicle screw positioned within the lumbar vertebra according to one aspect of the present invention.

FIG. 10 illustrates the first pedicle screw 12 placed from the right side 126 on the posterior side 122 of the vertebra 118. It will be appreciated that the exact placement and size of the first pedicle screw 12 relative to the vertebra 118, as shown and disclosed, herein may be enlarged or reduced proportionately depending upon the characteristics of the vertebra 118 and the goals of the vertebral stabilization assembly 10. However, the first pedicle screw 12 is preferably secured in the pedicle portion of the vertebra 118 such that the distal end 102 of the first pedicle screw 12 is coupleable to the guide member 150 on the left side 128 on the anterior side 124 adjacent the midline 178 of the vertebra 118.

In some aspects, the guide member 150 may be provided with a rotational coupling 190 such as a recess or opening in the offset member 154 of the guide member 150. The rotational coupling 190 may be adapted as an opening to receive a tool or device for obtaining leverage on the guide member 150 for rotation of the guide member 150. It will be appreciated that while the first pedicle screw 12 may be provided with indicia or other markings on the head 60 of the first pedicle screw 12 for determining the location and disposition of the engaging portion 22 of the first pedicle screw 12, a surgeon may have difficulty determining from the posterior side 122 of the vertebra 118 the optimum location for placement of the connecting screw, such as the first connecting screw 40.

Once the patient has been rotated and the guide member 150 connected to the first pedicle screw 12 on the anterior side 124 of the vertebra 118, only then will the surgeon be able to determine the preferable placement of the first connecting screw 40 relative to the body of the vertebra 118. In the event the first pedicle screw 12 is not aligned preferably for the first connecting screw 40, by use of the rotational coupling 190, such as with a tool connected thereto, the surgeon may rotate the guide member 150 and the first pedicle screw 12 rigidly connected thereto, via the locking screw 184, to obtain the optimum placement of the first connecting screw 40 into a desired point in the body of the vertebra 118. In other embodiments, the guide member 150 may not include the rotational coupling 190 and, as such, this rotational alignment may be achieved by grasping and rotating the offset member 154 or other portions of the guide member 150.

Once this optimum positioning has been obtained by rotation using the rotational coupling 190 the tool coupled to the rotational coupling 190 may be removed and a drill or other tool may be utilized and aligned via the alignment member 156 for drilling an opening into the body of the vertebra 118 at the desired location. Thereafter, the locking screw 184 and a guide member 150 may be removed for connection of the first connecting screw 40 to the engaging portion 22 of the first pedicle screw 12.

It will be appreciated that the locking screw 184 may be connected in a variety of manners to the coupling portion 152 of the guide member 150 to obtain a corresponding rotation of the guide member 150 with the first pedicle screw 12 for these rotational purposes which will readily suggest themselves to one of ordinary skill in the art and are within the spirit and scope of the present invention.

Figure 11:
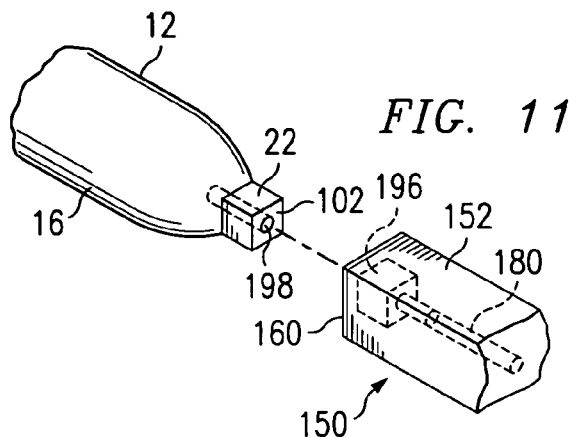
FIG. 11 is a perspective view illustrating yet another aspect of the connection of the pedicle screw with the guide member constructed in accordance with the present invention.

FIG. 11 illustrates another aspect of the connection of the first pedicle screw 12 to the coupling portion 152 of the guide member 150. As previously discussed above, a variety of methods exist for connecting the coupling portion 152 with the coupling portion 100 of the first pedicle screw 12. In the present aspect illustrated in FIG. 11, the coupling portion 100 of the first pedicle screw 12 is a substantially rectangular member extending therefrom the shaft 16 of the first pedicle screw 12.

The coupling portion 152 of the guide member 150, in the present aspect, is provided with a substantially rectangular opening 196 in the first end 160 of the coupling portion 152. The substantially rectangular opening 196 is sized to matingly receive the rectangular coupling portion 100 to achieve a fitted coupling there between. In this aspect, the coupling portion 100 may be provided with a threaded opening 198 on the distal end 102 of the first pedicle screw 12. In this manner, the channel 180 extending there through the coupling portion 152 may be provided to guide a connecting member, such as the locking screw 184 or other engaging structure, to be threadingly received by the threaded opening 198 in the distal end 102 of the first pedicle screw 12.

In this manner, the combination of the locking mechanism, such as the locking screw 184, as well as the rectangular configuration of the coupling portion 100 of the first pedicle screw 12 with the substantially rectangular opening 196 in the first end 160 of the coupling portion 152 promotes an accurately engaged connection of the guide member 150 with the first pedicle screw 12. It should be appreciated that in other aspects the threaded opening 198 and the channel 180 may be eliminated and only the mating connection of the rectangular coupling portion 100 of the first pedicle screw 12 with the substantially rectangular opening 196 of the coupling portion 152 will be sufficient for this connection.

It will be appreciated that the configuration illustrated in the current aspect promotes a sufficient engagement of the guide member 150 to the first pedicle screw 12 to achieve engaging rotation of the first pedicle screw 12 by the guide member 150 when such adjustment for alignment purposes of the first pedicle screw 12 is desirous. It should be appreciated that while the coupling portion 100 of the current aspect is shown as substantially rectangular in configuration as is the substantially rectangular opening 196 of the coupling portion 152 of the guide member 150, a variety of other configurations such as, but not limited to, triangular configurations, will readily suggest themselves to one of ordinary skill in the art and are within the spirit and scope of the present invention, as are a variety of other coupling connections between the coupling portion 152 and the first pedicle screw 12 which may be utilized to achieve these purposes.

Figure 12:
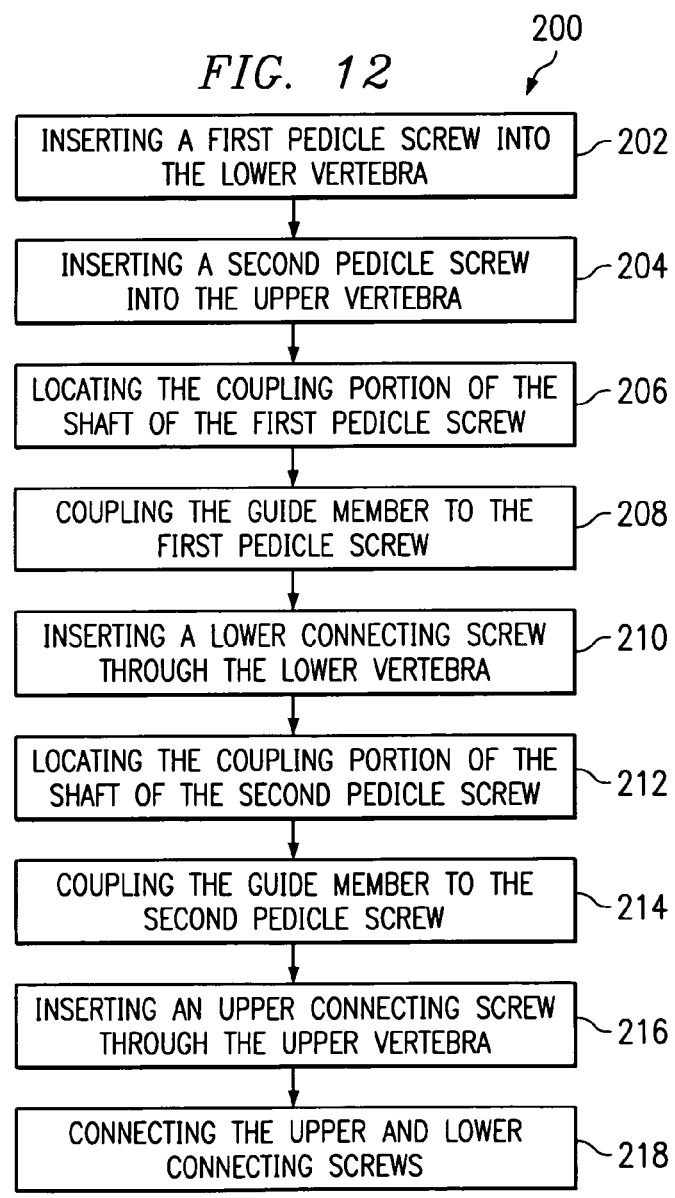
FIG. 12 is a flow chart illustrating a method for stabilizing vertebrae from the anterior side of the vertebrae utilizing the vertebral stabilization assembly according to another aspect of the present invention.

FIG. 12 is a flow chart illustrating a method 200 for stabilizing an upper and lower vertebra 118A and 118B, substantially similar to the vertebra 118 illustrated in FIGS. 5 and 7, from an anterior side 124 of the vertebra 118A and 118B using the vertebral stabilization assembly 10 in accordance with the present invention. The method includes, at a block 202, inserting the first pedicle screw 12 into the lower vertebra 118B through the pedicle 120 and into the body of the lower vertebra 118B from a posterior side 122 of the lower vertebra 118B. The first pedicle screw, as previously described above, includes the shaft 16 provided with the threaded portion 18 operable to threadingly engage the lower vertebra 118B. The shaft 16 of the first pedicle screw 12 is provided with the engaging portion 22 that is operable to receive the first connecting screw 40. The shaft 16 of the first pedicle screw 12 further has the coupling portion 100 that is operable to couple with the guide member 150.

The method further includes, at a block 204, inserting a second pedicle screw 14 into the upper vertebra 118A through the pedicle 120 and vertebral body of the upper vertebra 118A from the posterior side 122 of the upper vertebra 118A. The second pedicle screw 14 including the shaft 30 provided with the threaded portion 32 operable to threadingly engage the upper vertebra 118A. The shaft 30 of the second pedicle screw 14 provided with an engaging portion 36 operable to receive the second connecting screw 42. The shaft 30 of the second pedicle screw 14 having a coupling portion 100, substantially similar to the coupling portion 100 of the first pedicle screw 12, to couple with the guide member 150.

The first and second pedicle screws 12 and 14 are preferably placed on the posterior side 122 on the right side 126 of the upper and lower vertebra 118A and 118B, respectively. It will be appreciated that in one aspect the present invention may be utilized preferably with respect to the lumbar vertebra, while in other embodiments the present invention may be preferably utilized with regard to the thoracic vertebra.

At a block 206, the method includes locating the coupling portion 100 of the shaft 16 of the first pedicle screw 12 from the anterior side 124 of the lower vertebra 118B. As previously discussed, in one aspect the pedicle screw 12 of the present invention may be provided with the cannulated shaft 16 having the passageway 110 extending through the shaft 16 of the first pedicle screw 12. In this aspect a tool, such as a drill operable to drill through a portion of the lower vertebra 118B, may be extended through the passageway 110 of the shaft 16 of the first pedicle screw 12. The tool may be used to drill through a portion of the lower vertebra 118B such that the tool extends partially through the anterior side 124 at the lower vertebra 118B. Similarly, the second pedicle screw 14 may be similarly provided with the passageway 110 for passing the tool there through to drill through a portion of the upper vertebra 118A such that the drill extends at least partially through the anterior side 124 of the upper vertebra 118A.

At a block 208 the method includes coupling the guide member 150 to the coupling portion 100 of the shaft 16 of the first pedicle screw 12 from the anterior side 124 of the lower vertebra 118B. In one aspect the coupling of the guide member may be more readily accomplished after an opening has been drilled through to the anterior side 124 of the lower vertebra 118B. The method further includes, at a block 210, inserting the lower connecting screw, such as the first connecting screw 40, through the anterior side 124 of the lower vertebra 118B using the guide member 150. As previously discussed, the guide member is a useful tool for aligning the alignment member 156 of the guide member 150 and correspondingly the first connecting screw 40 with the engaging portion 22 of the first pedicle screw 12.

The method further provides, at a block 212, locating the coupling portion 100 of the shaft 30 of the second pedicle screw 14 from the anterior side 124 of the upper vertebra 118A. The method further provides, at a block 214, for coupling the guide member 150 to the coupling portion 100 of the shaft 30 of the second pedicle screw 16 from the anterior side 124 of the upper vertebra 118A.

At a block 216, the method includes inserting an upper connecting screw, such as the second connecting screw 42 through the anterior side 124 of the upper vertebra 118A utilizing the guide member 150 for proper alignment. The method also provides, at a block 218, for connecting the upper and lower connecting screws, such as the first and second connecting screws 40 and 42, to the connecting member 50 for stabilization of the upper and lower vertebra 118A and 118B.

FIG. 13 illustrates another aspect of the first pedicle screw 12 having a reinforced portion 230 provided on the shaft 16. The reinforced portion 230 of the shaft 16 provides additional structural stability for connection of the connecting screw, such as the first connecting screw 40, to the engaging portion 22 to ensure a rigid and stable connection of the first connecting screw 40 to the first pedicle screw 12. The reinforced portion 230 is shown having a diameter 232 that is greater than a diameter 234 of a first threaded portion 236 of the shaft 16. In this manner, it is readily apparent that the reinforced portion 230 having a greater diameter 232 will provide additional structural stability and support for connection of the first connecting screw 40 with respect to the smaller diameter 234 of the first threaded portion 236 of the shaft 16. The first threaded portion 236 of the shaft 16 is provided with a plurality of threads 238 connected to and extending from the shaft 16 of the first pedicle screw 12. It can be seen that the diameter 232 of the reinforced portion 230 is about equal to a diameter 240 measured from an outermost edge of the plurality of threads 238 of the first threaded portion 236.

As the first pedicle screw 12 is threadingly engaged into the pedicle portion of the vertebra, such as the first vertebra 20, the first threaded portion 236 will threadingly engage and retain the first pedicle screw 12 within the first vertebra 20. In the present embodiment the reinforced portion 230 is not provided with threads, however, in other embodiments the reinforced portion may be provided with threads similar to the plurality of threads 238 or threads extending less far from the reinforced portion 230 than the plurality of threads 238 extend from the first threaded portion 236 of the shaft 16. In one aspect, the diameter 232 of the reinforced portion 230 is about 6.5 millimeters. However, in other embodiments the diameter 232 of the reinforced portion 230 may be greater or less than 6.5 millimeters as may be necessary to properly engage the shaft 16 of the first pedicle screw 12 in the first vertebra 20.

The shaft 16 of the first pedicle screw 12 is further provided with a second threaded portion 242 having a plurality of threads 244 for engaging the first vertebra 20. In the present aspect, the diameter 232 of the reinforced portion 230 is less than the diameter 246 measured from an outermost edge of the plurality of threads 244 provided on the second threaded portion 242. As the first pedicle screw 12, of the present aspect, is engaged into the first vertebra 20, the first threaded portion 236 will threadingly engage the pedicle portion and thereafter an interior vertebral body portion of the first vertebra 20. As the reinforced portion 230 of the first pedicle screw 12 follows behind the first threaded portion 236, the reinforced portion 230 may have the affect of smoothing the threading engagement within the vertebral body. For this reason, it may be advantageous to provide the plurality of threads 244 having a greater diameter 246 for providing additional threading engagement of the first pedicle screw. In other aspects (not shown) frictional engaging surface structure, such as small or low profile threads, may be provided on the reinforced portion 230 for frictionally engaging the inner vertebral body at the first vertebra 20.

In the present aspect, the diameter 246 of the plurality of threads 244 may be about 7.0 millimeters to achieve additional threading engagement of the second threaded portion 242 of the shaft 16 for stable engagement of the first pedicle screw 12 within the first vertebra 20. It will be appreciated, however, that in other aspects (not shown) the diameter 246 of the plurality of threads 244 may be of larger or smaller diameter or may be of a similar or smaller diameter than the diameter 232 of the reinforced portion 230 and be adequate for these purposes. Furthermore, in other aspects (not shown) the diameter 234 of the first threaded portion 236 of the shaft 16 may be the same or larger diameter than that of the diameter 232 of the reinforced portion 230. The reinforced portion 230 of the shaft 16 provides significant additional structural stability for connection of the first connecting screw 40 to the first pedicle screw 12 via the engaging portion 22. While the length of the reinforced portion 230 relative to the length of the entire shaft 16 of the first pedicle screw 12 is shown in relative proportion according to the present aspect, the reinforced portion 230, according to other aspects (not shown), may be of significantly greater length and diameter or having a smaller length and diameter relative to the shaft 16 of the first pedicle screw 12 and are within the spirit and scope of the present invention as disclosed and described herein.

FIG. 14 illustrates a perspective view of another aspect of the pedicle screw 12 wherein the shaft 16 is provided with at least a first groove 250 extending a distance along the shaft 16 of the first pedicle screw 12. In the present aspect, a plurality of grooves 250 are shown adjacent a plurality of raised threaded portions 252. The raised threaded portions 252 are provided for threadingly engaging the first vertebra 20 for securing the first pedicle screw 12 to the first vertebra 20. The one or more grooves 250 are provided for engaging the first pedicle screw 12 by a tool which will be discussed in greater detail hereinafter with respect to FIGS. 17 and 18. In certain circumstances it may be useful or necessary to rigidly retain the first pedicle screw 12 from the anterior side of the first vertebra 20, such as when connecting the first connecting screw 40 to the first pedicle screw 12. The one or more grooves 250 provided on the shaft 16 promotes engagement of the first pedicle screw 12 by a tool near the distal end 102 of the shaft 16.

FIG. 15 illustrates a cross section of the first pedicle screw 12 illustrated in FIG. 14 taken along a line 15-15 thereof. In this view, the one or more grooves 250 provided on the shaft 16 of the first pedicle screw 12 can be seen with respect to their relationship to the raised threaded portions 252. This configuration is useful for promoting engagement of a tool for connecting near the distal end 102 of the first pedicle screw 12. Although the grooves 250 are shown as generally rounded in configuration extending a distance along the length of the shaft 16 it will be appreciated that in other embodiments (not shown) the grooves 250 may be angular, such as rectangular or triangular in configuration, and having a wider or narrower width 254 which are within the spirit and scope of the present invention as disclosed and described herein.

In this view, it can be seen that a number of grooves 250 such as two or four grooves 250 may promote improved engagement by a tool of the first pedicle screw 12 near the distal end 102, however, any number of grooves 250 may be utilized and are within the spirit and scope of the present invention.

It will be appreciated that the configuration of the first pedicle screw 12 illustrated having one or more grooves 250 extending a distance along the length of the shaft 16 may also be utilized with respect to the configuration of the first and second connecting screws 40 and 42. In this manner, a tool may be utilized to connect to the second end 64 of the first connecting screw 40 for inserting the first connecting screw 40 into the engaging portion 22 of the first pedicle screw 12, as well as for removal of the first connecting screw 40 from the engaging portion 22 of the first pedicle screw 12.

From time to time it may be necessary to remove portions of the vertebral stabilization assembly 10 of the present invention from the patient and it will become necessary for the first connecting screw 40 and the first pedicle screw 12 to be configured so as to be easily removable. It will be appreciated that metal tightly connected frequently galls or becomes frozen. In this manner, configuration of the first pedicle screw 12 and the first connecting screw 40 having, for example, grooves 250 and other similar configurations, as previously discussed, and utilization of a tool adapted to engage the grooves 250 along the shaft 16 of the first pedicle screw 12, for example, will be beneficial for obtaining the necessary leverage for installation and removal purposes.

FIG. 16 illustrates a cap 260 configured to be connected near the distal end 102 of the first pedicle screw 12. The cap 260 may be constructed from a variety of materials, such as a rigid or non-rigid plastic or polymeric material, metallic or other materials adapted for connection to the first pedicle screw 12 for penetration through the body of the first vertebra 20. In the present aspect it can be seen that the first end 262 of the cap 260 is substantially conically shaped for promoting penetration of the first pedicle screw 12 through the first vertebra 20. The cap 260 is advantageously provided where the first pedicle screw 12 is provided with a flat surface 264 on the distal end 102 of the first pedicle screw 12 (see FIG. 14).

A flat surface 264 on the distal end 102 of the first pedicle screw 12 further promotes connection and engagement of a tool to the first pedicle screw 12 for purposes which will be discussed hereinafter. In this aspect, the cap 260 will be necessary to reduce or minimize any damage or aggravation caused by placement of the pedicle screw to any nerves or tissue in or about the area of the first vertebra 20, such as nerves positioned near the pedicle portion of the first vertebra 20.

The cap 260 is shown as a substantially conical member having an inner surface 266 that is provided with one or more notches 268 provided on the inner surface 266 of the cap 260. The notches 268 are configured to be tensioningly received by a recess 270 which may be provided on the shaft 16 of the first pedicle screw 12 as shown in FIG. 14. In this manner, the notches 268 are tensioningly received by one or more recesses 270 on the shaft 16 which retains the cap 260 sufficiently engaged near the distal end 102 of the first pedicle screw 12, as well as promoting easy removal of the cap 260 from the first pedicle screw 12. The cap 260 may then be easily removed after placement of the first pedicle screw 12 for attachment of the guide member 150, as well as a tool for retaining and stabilizing the first pedicle screw 12 near the distal end 102 of the first pedicle screw 12.

Figure 17:
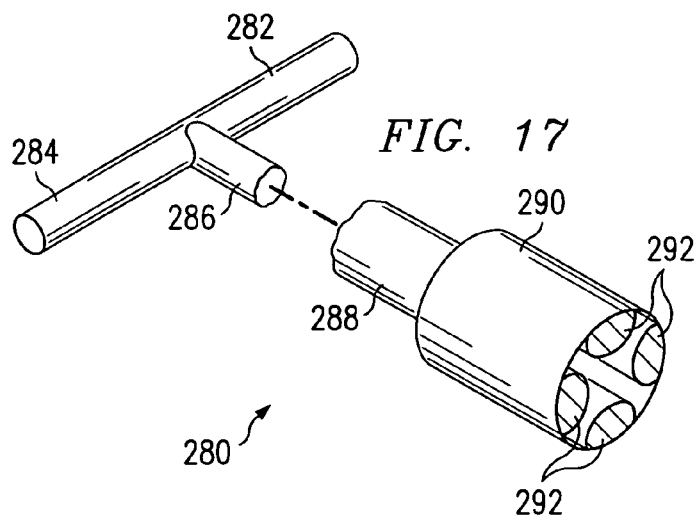
FIG. 17 is a perspective view of one aspect of a tool for connection near the distal end of the pedicle screw constructed in accordance with the present invention.

FIG. 17 illustrates a tool 280 constructed in accordance with one aspect of the present invention for stabilization of the first pedicle screw 12 and the connecting screws, such as the first connecting screw 40. The tool 280 is provided with a first end 282 having a handle 284 adapted to be grasped by the hand of an individual. The tool 280 is provided with a shaft 286 extending from the first end to a second end 288. The shaft 286 may be of sufficient length to easily utilize the tool 280 for connection and removal of the vertebral stabilization assembly 10 during the surgical process.

A connector 290 is provided on the second end 288 of the tool 280 and configured so as to receive, for example, the shaft 16 of the first pedicle screw 12 provided with one or more grooves 250 on the shaft 16. In this manner, the connector 290 is provided with mating notches 292 adapted to be received by the grooves 250 on the shaft 16 of the first pedicle screw 12.

Once positioned near the distal end 102 of the first pedicle screw 12, the mating notches 292 will receive and engage the first pedicle screw 12 so that the tool 280, when rotated by the individual, will have the affect of rotating the first pedicle screw 12, or, as previously discussed, for stabilizing and retaining the first pedicle screw 12 while removing or installing the connecting screws, such as the first connecting screw 40. As previously discussed, it may be necessary to utilize the tool 280 to stabilize the first pedicle screw 12, particularly when attempting to remove the rigid connection of the first connecting screw 40.

During the removal of the vertebral stabilization assembly 10, the first connecting screw 40 will likely be rigidly engaged in the engaging portion 22 of the first pedicle screw 12. When utilizing a first tool, such as the tool 280, to connect to for removal of the first connecting screw 40, it may be necessary to utilize a second tool, such as the tool 280, to engage the distal end 102 of the first pedicle screw 12 to retain the first pedicle screw 12 while removing the first connecting screw 40. Utilization of one or more of the tools 280 may be beneficial while installing, as well as removing the vertebral stabilization assembly 10.

Furthermore, it will be appreciated that in other aspects the connector 290 may be provided on an electric or pneumatic device such as a drill or other apparatus.

Figure 18:
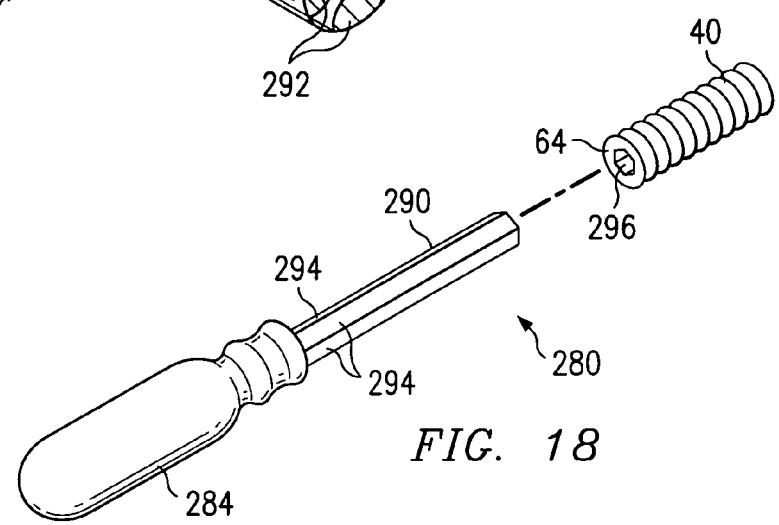
FIG. 18 is a perspective view of yet another aspect of the tool for use with the vertebral stabilization assembly of the present invention shown connecting to the connecting screw.

FIG. 18 illustrates another aspect of the tool 280 and a different aspect of the handle 284 as well as the connector 290. In this view, the handle 284 is more easily grasped by a single hand, such as the handle of a common screw driver, and the connector 290 is configured with a plurality of flat surfaces 294, such as ordinarily found in a wrench-wrench. In this manner, the first connecting screw 40 may be provided with an opening 296 configured to receive the connector 290 for engagement of the tool 280 with the first connecting screw 40.

A number of configurations of the opening 296 on the second end 64 may be utilized such as one or more grooves 250, and may be provided with associated tools, such as the tool 280 to establish a rigid engagement of the tool 280 to the connecting screw, such as the first connecting screw 40, and the first pedicle screw 12. It is within the scope of the present invention that the various configurations of the first pedicle screw 12 and the first connecting screw 40 may be interchanged along with the configurations of the tool 280 to promote maximum utility for installation and removal of the vertebral stabilization assembly. For example, the grooves 250 may be provided on the shaft 16 of the first pedicle screw 12, substantially as shown with respect to FIGS. 14 and 15, while the first connecting screw 40 may be provided with a wrench wrench-type opening 296 or vice versa.

In this manner, one or more configurations of tools may be utilized on one or more of the elements of the vertebral stabilization assembly 10 and are within the spirit and scope of the present invention as disclosed and described herein. Furthermore, it will be appreciated that the opening 296 provided on the first connecting screw 40 or on the distal end 102 of the first pedicle screw 12 may be tapped and threaded opening in a standard or reverse threaded manner for engagement of, for example, the connector 290 having a threaded connector 290 (not shown) for engagement of the tool 280 to the first connecting screw 40 or the first pedicle screw 12.

Also, for example, where the distal end 102 of the first pedicle screw 12 is substantially rectangularly shaped, such as in the aspect illustrated in FIG. 11, the connector 290 of the tool 280 may be configured to receive the rectangular distal end 102 of the first pedicle screw 12 or a rectangularly shaped second end 64 of the first connecting screw 40. Many other configurations of the distal end 102 of the pedicle screw, such as the first pedicle screw 12, and connecting screws, such as the first connecting screw 40, may be provided and associated tools 280 having connectors 290 for connection thereto and will readily suggest themselves to one of ordinary skill in the art and are within the spirit and scope of the present invention described and disclosed herein.

Furthermore, it is within the spirit and scope of the present invention that the first connecting screw 40 may be provided with a double-bolted configuration on the threaded portion 66 of the first connecting screw 40 and the connector 290 may be a socket-type connection to receive the bolt or bolts for removal of the first connecting screw 40 utilizing the tool 280.

Figure 19:
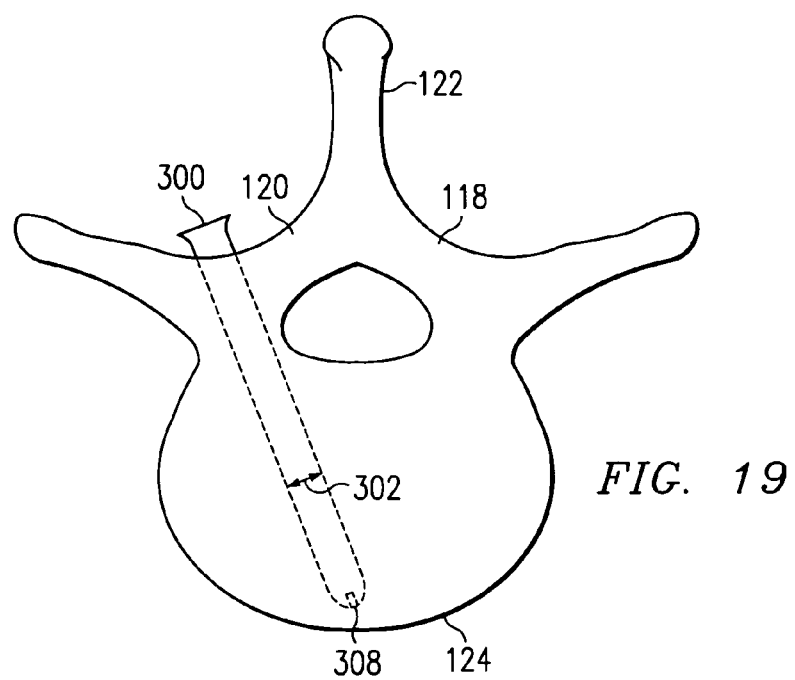
FIG. 19 is a top plan view of a bore screw according to one aspect of the present invention shown obliquely disposed in the vertebra.

FIG. 19 illustrates a bore screw 300 which may be utilized according to one aspect of the present invention. The bore screw 300 may be provided with threads (not shown) and may be placed obliquely from the posterior side 122 of the vertebra 118. The bore screw 300 may be sized such that the diameter 302 of the bore screw 300 is sized substantially similar to or smaller than the diameter of the pedicle screw, such as the first pedicle screw 12. However, it will be appreciated that in other aspects it may be advantageous for the diameter 302 of the bore screw 300 to be substantially similar in size to that of the first pedicle screw 12 or, in some instances, for the diameter 302 to be substantially larger.

The bore screw 300 is shown disposed in the pedicle 120 at a desirable angle extending through the vertebra 118. In this manner the bore screw 300 may be utilized to create a bore opening (not shown) that may be useful for placing the pedicle screw, such as the first pedicle screw 12, for placement of the pedicle screw from the anterior side 124 of the vertebra 118. In such a procedure the bore screw 300 may be percutaneously placed in the posterior 122 of the vertebra 118. Thereafter the patient may be rotated such that the anterior 124 of the vertebra 118 is exposed. The bore screw 300 may be provided with a coupling portion 308 adapted for attachment by a tool (not shown) for removal of the bore screw 300 through the anterior 124 side of the vertebra 118.

In other aspects, the bore screw 300 may be utilized from the anterior 124 for tapping the vertebra 118. In other aspects, the coupling portion 308 is adapted to engage the guide member 150 for determining alignment. For example, the guide member 150 may be attached to the coupling portion 308 of the bore screw 300 to determine the approximate location of the connecting screw, such as the first connecting screw 40, and where the second end 64 of the first connecting screw 40 will be exposed on the anterior 124 side of vertebra 118.

Attachment of the guide member 150 to the bore screw 300 provides another advantage of the present aspect in that it may be easily determined whether the bore screw 300 is placed at the appropriate location in the vertebra 118 or whether another placement will be necessary. This eliminates the need to place the pedicle screw, such as the first pedicle screw 12, and then determine whether the placement is acceptable.

Figure 20:
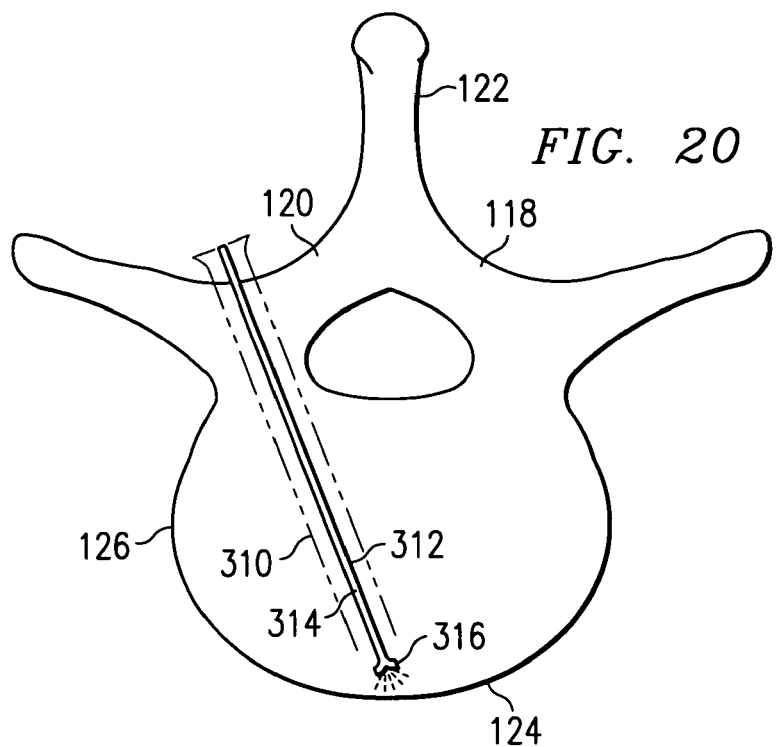
FIG. 20 is a top plan view of an indicator constructed in accordance with one aspect of the present invention disposed in a bore opening of the vertebra.

FIG. 20 illustrates a bore opening 310 which may have been created by the bore screw 300, or in other embodiments may have been created by a drill or other device capable of creating an opening in the vertebra 118. An indicator 312 is shown disposed in the bore opening 310. The indicator is provided with a shaft 314 and a light 316 provided on one end of the shaft 314. The light 316 may be a common LED (light emitting diode) or other light-emitting device which is suitable for these purposes, and may include laser light or laser light-emitting diodes.

The shaft 314 may be a substantially rigid shaft of sufficient length to extend down the length of the bore opening 310 and be operable to retain the light 316 and communicate sufficient electrical power to maintain the light 316 with power for driving the light 316. In other aspects, the shaft 314 may be a substantially flexible material such as wire or other flexible cording or material.

The indicator 312 is a useful device for indicating the location of the bore opening 310 from the anterior side 124 of the vertebra 118. As previously discussed, a number of soft tissues exist on the right side 126 on the anterior side 124 of the vertebra 118. For this reason, whether a bore screw 300 or a drill is utilized to create the bore opening 310 from the posterior side 122, it will be necessary in many cases to prevent penetration of the bore screw 300 or drill completely through the vertebra 118 on the anterior side 124 to prevent damage to the soft tissues on the anterior side 124. The indicator 112 provides an opportunity once the patient has been rotated to retract the soft tissues and identify the location of the bore opening 310 from the anterior side 124.

For example, the light 316 shown in the bore opening 310 will be perceptible by the surgeon from the anterior side 124 of the vertebra 118. The surgeon may then drill from the anterior side 124 to complete the bore opening 310. Where the bore screw 300 is utilized, the bore screw may be provided with a light, such as the light 316, provided on the distal end of the bore screw 300 and will be sufficient for these purposes. Once the light 316, whether provided on the indicator 312 or the bore screw 300, has been identified and the bore opening has been drilled to communicate with the anterior side 124 of the vertebra 118, the indicator 312 or bore screw 300 may then be removed from the anterior side. The indicator 314, such as when the light 316 is a high intensity LED or laser light, may be disposed near the posterior side 122 or only slightly within the bore opening 310 such that the light produced by the light 316 projects down through the bore opening 310 and is sufficient to identify the bore opening 310 from the anterior side 124 of the vertebra 118.

Furthermore, the indicator 312 may, in other aspects, be provided with a pneumatic or hydraulically operated capability for punching or extending through the anterior side 124 of the vertebra 118 when the indicator 312 is extended through the bore opening 310, such as by utilizing a drill. In this manner, the indicator 312 may be left in place in the bore opening 310 and after the patient has been rotated such that the anterior side 124 of the vertebra 118 has been exposed, the pneumatic or hydraulically-operated indicator 312 may be activated so as to extend through the anterior side 124 for communication into the bore opening 310.

The indicator 312 may be pulled through the anterior side 124 of the vertebra 118, and in instances where the shaft 314 is a flexible material, it may be severed from, for example, behind the patient, for easy removal through the anterior side 124. Where the bore screw 300 is utilized and still in place, a tool (not shown) may be connected to the coupling portion 308 of the bore screw 300 so that the bore screw 300 may be removed through the anterior side 124 of the vertebra 118. This is advantageous since it eliminates the rotation of the patient for removal of the bore screw 300 or the indicator 312. The elimination of a rotational procedure further reduces the time of the overall procedure and is another advantage of the present aspect of the vertebral stabilization assembly 10 invention disclosed herein.

Figure 21:
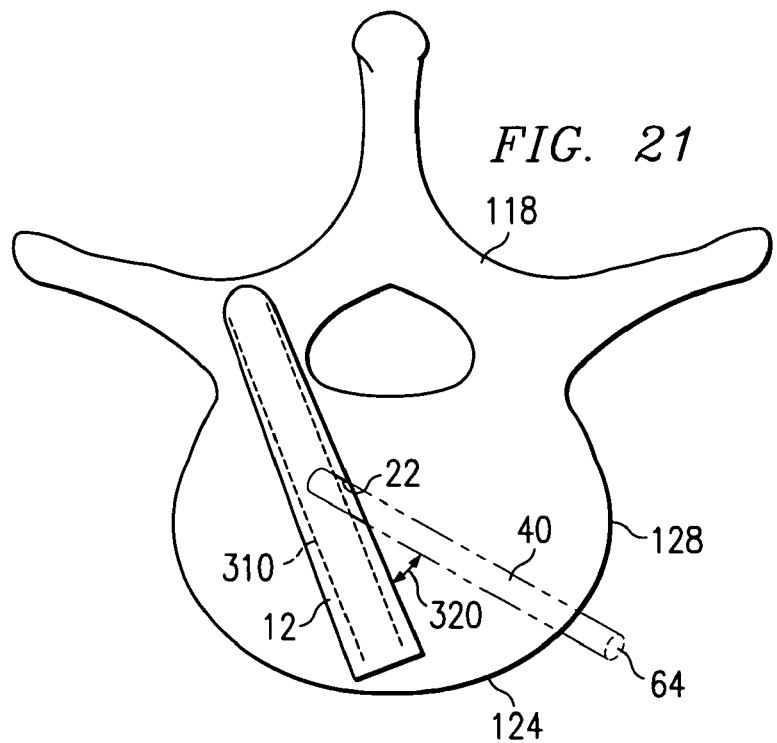
FIG. 21 is a top plan view of the pedicle screw for anterior placement according to yet another aspect of the present invention shown with a distal end of the pedicle screw anchored in the pedicle portion of the vertebra.

FIG. 21 illustrates another aspect of the vertebral stabilization assembly 10 of the present invention. In this aspect the pedicle screw, such as the first pedicle screw 12, is placed in the vertebra 118 from the anterior side 124. By utilizing the bore opening 310, the pedicle screw 12 may be more easily and accurately placed into the vertebra 118 from the anterior side 124. Placement of the first pedicle screw 12 from the anterior side 124 has a number of advantages including that the angle of placement has been previously defined by the bore opening 310. This allows for selection of the first pedicle screw 12 having an engaging portion 22 provided with the appropriate angle 320 with respect to connection of the connecting screw, such as the first connecting screw 40 (shown in phantom).

It will be appreciated that the exact angle of placement of the first pedicle screw 12 and resulting angle 320 with respect to the engaging portion 22 and first connecting screw 40 will be unknown until such time that the first pedicle screw 12 is actually in place in the vertebra 118. By previously providing the bore opening 310, the proper pedicle screw may be selected based upon the desired resulting angle 320 sought for the resulting placement of the first connecting screw 40. That is, it may be advantageous in certain instances to provide the second end 64 of the first connecting screw 40 at a specific location on the left side 128 on the anterior side 124 of the vertebra 118. Unless the first pedicle screw 12 is exactly placed, the resulting location of the second end 64 of the first connecting screw 40 may be significantly different than that desired. For this reason, a number of pedicle screws may be advantageously provided to the surgeon each having a different length and a different engaging portion 22 with respect to the angle of connection of the first connecting screw 40 to the engaging portion 22. By having a number of choices available to the surgeon, and based upon the angle of the bore opening 310, the first pedicle screw 12 may be selected as having an engaging portion 22 that will provide the angle 320 that will result in the second end 64 of the first connecting screw 40 being positioned at the desired location on the anterior side 124 of the vertebra 118.

Anterior side 124 placement of the first pedicle screw 12 within the vertebra 118 provides numerous additional advantages including the dimensions of the first pedicle screw 12 and resulting stability that may be achieved from such placement. For example, the first pedicle screw 12, such as that illustrated in FIGS. 4 and 13, may be readily utilized for these purposes, and may achieve advantageous stabilization by being placed from the anterior 124 side of the vertebra 118. For example, with respect to the first pedicle screw 12 illustrated in FIG. 13, it can be seen that the diameter 232 of the reinforced portion 230 is slightly smaller than the diameter 246 of the plurality of threads 244 according to one aspect.

Since the reinforced portion 230 will not obtain the threading engagement, it is necessary for the plurality of threads 244 of the first pedicle screw 12 to be slightly larger to achieve a satisfactory anchoring and threading engagement of the first pedicle screw 12. Otherwise, the reinforced portion 230 might have the affect of smoothing the opening such that the plurality of threads 244 do not successfully engage within the vertebra 118.

Conversely, anterior side 124 placement of the pedicle screw allows for the plurality of threads 238 near the distal end 102 of the first pedicle screw 12 to be of a maximum diameter 240 for optimum anchoring and stabilization of the pedicle screw within the vertebra 118 and particularly within the pedicle portion 120. At the same time, the diameter 232 of the reinforced portion 230 may be of a maximum diameter for reinforcement to optimize the connection and engagement of the first connecting screw 40 and such structure will not reduce or minimize the engagement of the first pedicle screw 12 with the vertebra 118. The reason for this is that the plurality of threads 238 will be in front of the reinforced portion 230 when anteriorly placed versus behind the reinforced portion 230, as is the case with the plurality of threads 244 when the pedicle screw 12 is posteriorly placed. In one aspect, diameter 232 of the reinforced portion 230 is similarly sized relative to the diameter 246 of the plurality of threads 244 or any other threads provided on the shaft 16. However, numerous configurations of shaft 16 sized and thread sizes will readily suggest themselves to one of ordinary skill in the art and are within the spirit and scope of the present invention.

It should be appreciated that a variety of configurations of pedicle screws have been disclosed and shown herein and any of the various configurations may be utilized both for posterior placement of the first pedicle screw 12 as well as for anterior placement of the first pedicle screw 12. Furthermore, it will be appreciated that a number of tools, such as the tool 280 illustrated in FIGS. 17 and 18, have been shown and described and may be readily implemented on the first pedicle screw 12 for anterior placement.

FIG. 22 illustrates the first pedicle screw 12 connecting to the guide member 150 for proper alignment of the connecting screw, such as the first connecting screw 40 to the first pedicle screw 12. In one aspect, the present invention is directed to the vertebra stabilization assembly 10 wherein the complete procedure may be accomplished from the anterior side 124 of the vertebra 118. The procedure for such placement may include drilling a hole utilizing a drill or other device or implement through the outer surface of the anterior side 124 of the vertebra 118 to penetrate the hard outer bone surface.

Thereafter utilizing technology typically employed for such purposes, such as an image intensifier, x-ray and templates, and/or other stealth technology, a K-wire or other drill or penetrating implement may be utilized to penetrate in a direction toward the posterior side 122 along a line 326. The K-wire may be obliquely placed through the vertebral body into the pedicle 120 on the right side 126. A cannulated drill may be utilized to drill over the K-wire to ream out a hole or opening for placement of the first pedicle screw 12 therein. The drill and K-wire may be removed and the first pedicle screw 12 may be anteriorly placed in the drilled opening substantially along the line 326 for proper placement of the first pedicle screw 12 in the vertebra 118. This aspect, as previously discussed, advantageously provides for selecting, in advance, the proper pedicle screw, such as the first pedicle screw 12, having the engaging portion 22 to achieve the desired angle of connection of the connecting screw, such as the first connecting screw 40.

Another advantage of anterior placement of the first pedicle screw 12 is that it provides the opportunity for stabilization from the posterior side 122 when such may be desirable. In this aspect, the first pedicle screw 12, such as that illustrated and previously disclosed herein in a number of different embodiments, may be utilized by placement initially from the anterior side 124 such that the distal end 102 is anchored substantially in the pedicle 120 portion of the vertebra 118. Thereafter, the first pedicle screw 12 may be utilized for connection of connecting members, such as the connecting member 50, for standard posterior anchoring and stabilization when such is necessary because of a failure to achieve adequate stabilization from the anterior side 124 as preferably provided herein.

Under the preferred anterior stabilization and when the first pedicle screw 12 is placed from the anterior side 124 of the vertebra 118, the first pedicle screw 12 is provided with a coupling portion 100 near the head 60 of the first pedicle screw 12, substantially as shown in FIG. 22.

Utilization of the vertebral stabilization assembly 10 according to the aspect illustrated in FIG. 22, has the additional advantage of completely eliminating rotation of the patient during the procedure. However, it will be appreciated that there may be certain instances when it is necessary or useful to rotate the patient for posterior access to the vertebra 118 and such rotation will not reduce or detract from the advantages of the vertebral stabilization assembly 10 of the present invention in that a significant portion or all of the procedure may be achieved from the anterior side 124 of the vertebra 118. This presents a significant advantage in that rotation of the patient takes considerable time and eliminating the necessity for such rotation shortens the time period required for the procedure.

Once the first pedicle screw 12 has been placed on the anterior side 124 of the vertebra 118 substantially as shown and discussed above with respect to FIG. 22, the guide member 150 may be connected to the first pedicle screw 12 at the coupling portion 100 in a manner similar to that previously shown and described with respect to the coupling portion 100 and a guide member 150. Utilization of the guide member 150 as well as the connection of the connecting screws, such as the first and second connecting screws 40 and 42, as well as the bracket 50 remains substantially similar to that previously shown and described herein.

It should be appreciated that it is within the scope of the present invention to anteriorly place the first pedicle screw 12 on the left anterior side 124, similar to that shown in FIG. 8 except the first pedicle screw 12 is placed from the anterior instead of posterior of the vertebra 118. In fact, in some instances, anterior placement on the left side may be advantageous. The reason that this placement may be preferable is that the angle of the shaft 16 of the first pedicle screw 12 is more shallow with respect to the first connecting screw 40. This shallower angle will require a smaller guide member 150 and result in the surgery being performed in a smaller physical area. Since space is limited in the cavity of the patient, this configuration may be useful in some circumstances. Also, anterior placement of the pedicle screw on the left side may be utilized as a salvage when the right side becomes fractured or the desired stabilization is not obtained on the right side of the vertebra 118.

FIG. 23 illustrates another aspect of the engaging portion 22 of the first pedicle screw 12 according to another aspect of the present invention. As previously discussed, depending upon the oblique angle of placement of the first pedicle screw 12 with respect to the vertebra 118, the angle of engagement of the first connecting screw 40 with the first pedicle screw 12 may necessarily vary. For this reason, the present invention is further directed to an engaging opening 330 wherein the engaging portion 22 is retained within the shaft 16 of the first pedicle screw 12.

In this manner, the engaging portion 22 may be retained in the manner such that the engaging portion 22 may be rotated to receive the first connecting screw 40 at various angles 332. Although two angles 332 are shown, a variety of angles may be achieved utilizing the present aspect of the engaging portion 22. The engaging portion 22 may be retained on bearings or other floating structural devices within the engaging opening 330, such that when the first connecting screw 40 is coupled with the engaging portion 22, the engaging portion 22 becomes fixed with respect to the initial angle 332 of engagement.

Such variable positioning of the engaging portion 22 can further be obtained by a hinge or a latch connected to the engaging portion 22 for hinging or latching rotation at the engaging portion 22 within the engaging opening 330. Also, the engaging portion 22 may be provided on a rotational or ratcheted body (not shown) within the engaging opening 330. It will be appreciated that a wide variety of structures may be utilized for obtaining and achieving an engaging portion, such as the engaging portion 22 to obtain various angulation, such as the angles 332 of connection of the first pedicle screw 12 relative to the first connecting screw 40 and are well known to those of ordinary skill in the art and are within the spirit and scope of the present invention and for brevity will not be further discussed herein.

The advantage of the engaging portion 22 adapted for angular adjustment is that it eliminates the need for a number of pedicle screws having different engaging portions with different angles for connection to the first connecting screw 40. However, it should be appreciated that in other aspects the engaging portion 22 is a fixed and rigid structure for engagement of the first connecting screw 40 and, as such, a plurality of pedicle screws may be necessary each having a different angle of engagement of the first connecting screw 40 at the engaging portion 22 based upon the angle of placement of the first pedicle screw 12 in the vertebra 118.

Furthermore, according to other aspects of the present invention, it is anticipated that a variety of pedicle screws, such as the first pedicle screw 12, having significantly different lengths will be utilized for various adaptations and placements. Also, a variety of pedicle screws, such as the first pedicle screw 12, where the fixed engaging portions 22 is available in variety of angles of connection of the connecting screw relative to the shaft 16 of the first pedicle screw 12.

FIG. 24 illustrates another aspect of the present invention of the first pedicle screw 12, wherein only a portion of the shaft 16 of the first pedicle screw 12 is illustrated. In this aspect the shaft 16 is provided with at least one non-continuous thread 336 extending circumferentially about the shaft 16 of the first pedicle screw 12. In this manner, a first portion 338 of the non-continuous threads 336 extend circumferentially about a portion of the shaft 16 while a second portion of the non-continuous threads 336 extend about a second portion of the shaft 16.

A gap 342 is disposed between the first portion 338 and the second portion 340 of the non-continuous threads 336. The gap is a portion of the shaft 16 that is not provided with threads and may be of various circumferential dimensions and be suitable for these purposes. It will be appreciated that frequently the first pedicle screw 12 and particularly the threads on the shaft 16 may cause aggravation and irritation to nerves adjacent the vertebra 18. Once it has been determined that a nerve is aggravated by the placement of the first pedicle screw 12, adjustment or replacement of the first pedicle screw 12 is necessitated. Frequently, this requires completely removing and relocating the first pedicle screw 12 according to another oblique angle in the vertebra 118. By providing the first pedicle screw 12 having one or more of the non-continuous threads 336, according to the present aspect, aggravation of the nerve may be potentially alleviated by only a minor rotation of the first pedicle screw 12 since it is likely that the thread on the shaft 16 may be causing the irritation or aggravation of the nerve. Thus, upon a minor or slight rotation of the first pedicle screw 12 the gap 342 will replace, for example, the non-continuous threads 336 and alleviate the aggravation of the nerve and, thus, eliminate the necessity for completely removing and repositioning the first pedicle screw 12. It will be appreciated that the position and distribution of the non-continuous threads 336 with respect to their symmetrical placement may be altered or modified and are within the spirit and scope of the present invention as described and disclosed herein and will readily suggest themselves to one of ordinary skill in the art.

FIG. 25 illustrates another aspect of the vertebral stabilization assembly 10 having dual pedicle screws 400a and 400b for placement in the vertebra 118 to provide additional stability. The pedicle screws 400a and 400b are substantially similar to the first and second pedicle screws 12 and 14 in many aspects. The dual pedicle screws 400a and 400b, however, are provided with engaging portions 402a and 402b relative to one another such that a connecting screw 404, substantially similar to the first connecting screw 40, may be connected to both the dual pedicle screws 400a and 400b. The connecting screw 404 may be provided with a first end 406 adapted to be received by the engaging portion 402a of the pedicle screw 400a. The connecting screw 404 is further provided with a shaft 408, at least a portion of which is operative to connect to the engaging portion 402b of the pedicle screw 400b. The dual pedicle screws 400a and 400b must be constructed and configured such that upon placement in the vertebra 118 pedicle screws 400a and 400b provide for such connection by the connecting screw 404.

In some aspects the engaging portion 402b of the pedicle screw 400b may be an opening sufficient to receive the connecting screw 404 through the opening, as well as for engaging the shaft of 408 of the connecting screw 404. It is readily apparent that this configuration of the dual pedicle screws 400a and 400b provides significant vertebral support and stability. Furthermore, although only the vertebra 118 is shown it should be understood that the present configuration, including the dual pedicle screws 400a and 400b and a connecting screw 404, may be utilized for placement in a plurality of vertebra to provide increased stabilization for a plurality of vertebra for the purposes previously discussed and disclosed herein.

In another aspect, the present invention provides a fixation tool 430 for properly aligning the dual pedicle screws 400a and 400b for placement in the vertebra 118. Accurate alignment and placement of the dual pedicle screws 400a and 400b, according to one aspect, may be advantageously provided by utilizing the fixation tool 430. The fixation tool 430 is provided with alignment members 432a and 432b to achieve the proper alignment of the dual pedicle screws 400a and 400b in the vertebra 118. The alignment members 432a and 432b may be similar to the alignment member 156 of the guide member 150 previously disclosed and described above.

It may be advantageous, according to other aspects, to provide indicia on the dual pedicle screws 400a and 400b to provide for the proper alignment of the pedicle screws 400a and 400b. In other aspects the fixation tool 430 may be unnecessary when employing x-ray, stealth, or other imaging technologies to ensure the accurate alignment and placement of the dual pedicle screws 400a and 400b. In other aspects, however, the fixation tool 430 may be used such that the dual pedicle screws 400a and 400b may be simultaneously placed to ensure the engaging portions 402a and 402b of the dual pedicle screws 400a and 400b, respectively, are in proper alignment for connection by the connecting screw 404.

The pedicle screws 400a and 400b may also utilize guiding and locating techniques, previously discussed above, such that the pedicle screws 400a and 400b may be placed posteriorly, percutaneously or otherwise, and the connecting screw 404 may be placed anteriorly. Once the pedicle screws 400a and 400b have been inserted, the patient may then be rotated. A guide member, such as the guide member 150 may be utilized for connection and alignment of the connecting screw 404, as previously discussed above.

Thus, the guide member 150 is coupled, for example, to the pedicle screw 400a such that the alignment member 156 is operable to properly align the connecting screw 404 for coupling to the dual pedicle screws 400a and 400b. This may include, as previously discussed, drilling a tap hole or other guiding hole for accurate placement and alignment of the connecting screw 404. In any event, the connecting screw 404 may then be connected to the dual pedicle screws 400a and 400b in a configuration substantially as illustrated in the present aspect.

FIG. 26 illustrates another aspect of the present invention utilizing dual pedicle screws 400a and 400b for anterior placement. It will be appreciated, as previously discussed, that one advantage of the present invention is placement of the pedicle screws from the anterior side 124 of the vertebra 118. The current aspect illustrates another embodiment of the fixation tool 430 having alignment members 432a and 432b for alignment of the dual pedicle screws 400a and 400b, respectively, from the anterior side 124 of the vertebra 118. The fixation tool 430 may also combine the alignment features of the guide member 150 (See FIG. 25) to achieve the proper alignment of the connecting screw 404 as well.

In one aspect, the fixation tool 430 may be implemented by determining the point 440 on the vertebra 118 to desirably place the connecting screw 404. A pin, tack or other means may be employed to position and orient the alignment portion 442 which will provide the proper alignment for the connecting screw 404. Once the desired placement for the connecting screw 404 has been located, the dual pedicle screws 400a and 400b may then be aligned and placed in the vertebra 118 utilizing the alignment members 432a and 432b of the alignment tool 430. In some aspects the alignment members 432a and 432b may be provided with an inner and an outer barrel (not shown) wherein the inner barrel may be utilized to drill a guide hole in the vertebra 118 and the outer barrel may then be used to guide the pedicle screws 400a and 400b into place.

Figure 27:
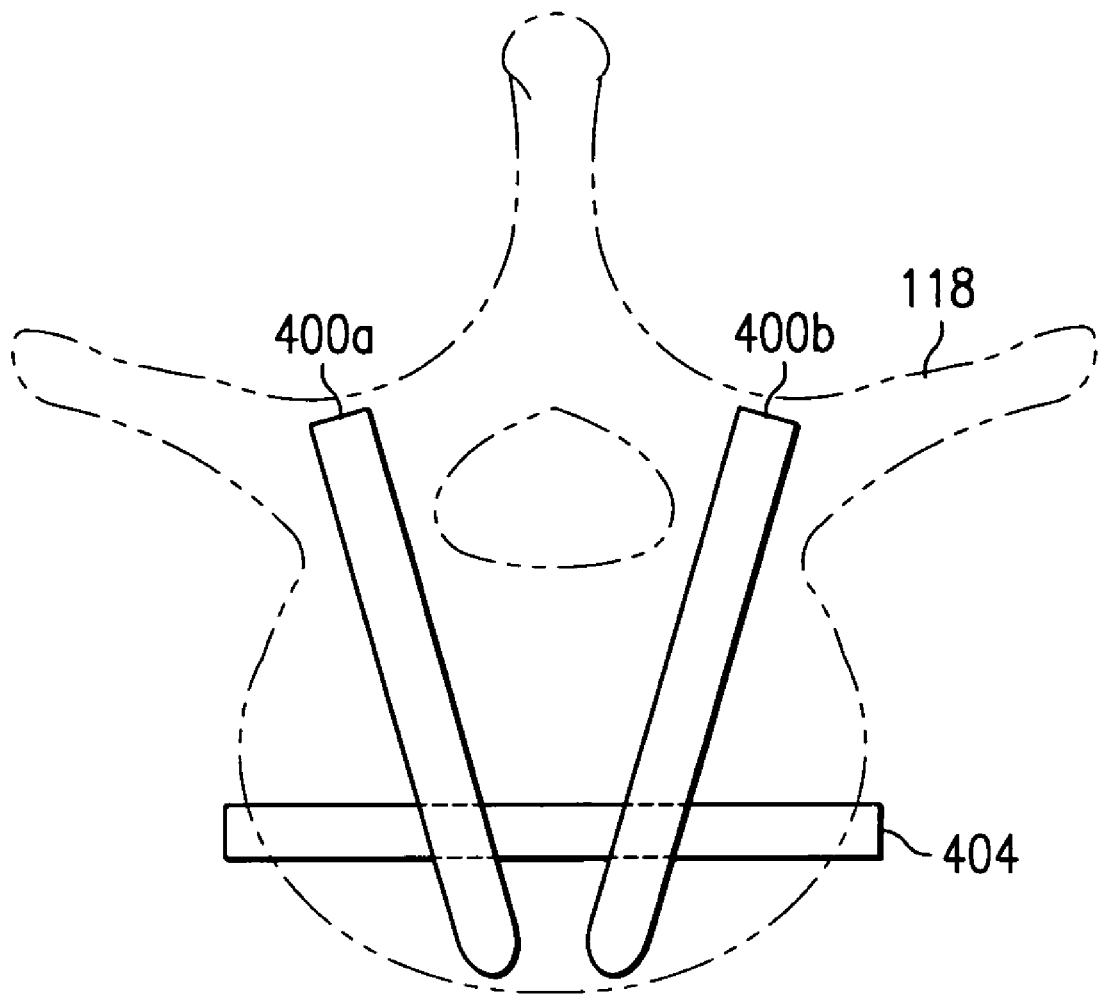
FIG. 27 is a top plan view according to one aspect of the present invention illustrating a connecting screw extending across the vertebra and connected to one or dual pedicle screws.

FIG. 27 illustrates another aspect of the present invention wherein the connecting screw 404 may be placed across the body of the vertebra 118. In many instances it may be advantageous to position the connecting screw 404 in such a manner for coupling of the connecting screw 404 to adjacent vertebra similarly stabilized. It is within the spirit and scope of the present invention that such placement of the connecting screw 404 may still utilize the additional stability provided by one or more pedicle screws 400a and 400b. The pedicle screw 400b is illustrated in phantom to denote that such placement of the connecting screw 404 may not necessitate placement of dual pedicle screws 400a and 400b and only one pedicle screw 400a may be sufficient to provide the desired stability in these instances.

Thus, it is apparent that there has been provided, in accordance with the present invention, a vertebral stabilization assembly and method that satisfies one or more of the advantages set forth above. Although the preferred embodiment has been described in detail, it should be understood that various changes, substitutions, and alterations can be made herein without departing from the scope of the present invention, even if all of the advantages identified above are not present. For example, the various embodiments shown in the drawings herein illustrate that the present invention may be implemented and embodied in a variety of different ways that still fall within the scope of the present invention.

Also, the techniques, designs, elements, and methods described and illustrated in the preferred embodiment as discrete or separate may be combined or integrated with other techniques, designs, elements, or methods without departing from the scope of the present invention. Other examples of changes, substitutions, and alterations are readily ascertainable by one skilled in the art and could be made without departing from the spirit and scope of the present invention.

What is claimed is:

1. A guide member comprising:
an offset member;
a coupling portion connected to the offset member, the coupling portion of the guide member configured to couple with a coupling portion of a vertebral screw disposed within a vertebra along a first longitudinal axis such that the guide member is rotatable about the first longitudinal axis; and
an alignment member connected to the offset member, the alignment member comprising an opening extending through at least a portion of the alignment member along a second longitudinal axis, wherein the second longitudinal axis intersects with the first longitudinal axis within the vertebra, wherein the opening is configured to receive a drilling device for drilling an opening in the vertebra along the second longitudinal axis such that a connecting screw later disposed within the opening in the vertebra is aligned for coupling with a portion of the vertebral screw within the vertebra.

2. The guide member of claim 1, wherein the coupling portion of the guide member is configured to couple with the coupling portion of the vertebral screw such that the offset member extends in a direction relative to the coupling of the coupling portion of the guide member to the coupling portion of the vertebral screw.

3. The guide member of claim 1, wherein the offset member comprises a first end and a second end, and wherein the first end of the offset member is connected to the coupling portion of the guide member and wherein the second end of the offset member is coupled to the alignment member.

4. The guide member of claim 3, wherein the offset member is positionable relative to the coupling of the coupling portion of the guide member with an end portion of the vertebral screw.

5. The guide member of claim 3, wherein the offset member arcuately extends from the coupling portion of the guide member.

6. The guide member of claim 1, wherein the coupling portion of the guide member couples to the coupling portion of the vertebral screw such that the offset member positions the alignment member substantially aligned adjacent the coupling portion of the vertebral screw.

7. The guide member of claim 6, wherein the alignment member substantially aligns adjacent an engaging portion of a shaft of the vertebral screw.

8. The guide member of claim 6, wherein the alignment member substantially aligns adjacent an opening on a shaft of the vertebral screw.

9. The guide member of claim 8, wherein the alignment member provides alignment for threading the connecting screw in the vertebra adjacent the opening in the vertebral screw.

10. The guide member of claim 8, wherein the alignment member provides alignment for attachment of the connecting screw to the vertebral screw.

11. The guide member of claim 1, wherein the alignment member further comprises a tubular member having a first end, a second end, and the opening extending through the tubular member from the first end to the second end.

12. The guide member of claim 11, wherein the opening extending through the tubular member is provided with a diameter sufficient to receive the connecting screw through the opening in the tubular member for alignment with an engaging portion of a shaft of the vertebral screw.

13. The guide member of claim 1, wherein the coupling portion of the guide member comprises a threaded member adjacent an end of the coupling portion, the threaded member operable to threadingly engage the coupling portion of the vertebral screw.

14. The guide member of claim 1, wherein the coupling portion of the guide member comprises an angularly configured opening to matingly receive an angularly configured end of the vertebral screw for attachment of the guide member to the vertebral screw.

15. The guide member of claim 1, wherein the coupling portion of the guide member comprises an angularly configured end to be matingly received by an angularly configured opening of the vertebral screw to attach the guide member to the vertebral screw.

16. The guide member of claim 1 further comprising a second coupling portion connected to the offset member, the second coupling portion of the guide member configured to couple with a coupling portion of a second vertebral screw disposed within a vertebra along a third longitudinal axis, wherein the second longitudinal axis intersects with the third longitudinal axis within the vertebra such that the connecting screw later disposed within the opening in the vertebra is aligned for coupling with portions of both the vertebral screw and the second vertebral screw within the vertebra.

* * * * *

UNITED STATES PATENT AND TRADEMARK OFFICE
CERTIFICATE OF CORRECTION

PATENT NO. : 7,645,280 B2
APPLICATION NO. : 11/146075
DATED : January 12, 2010
INVENTOR(S) : Paul A. Vaughan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 905 days.

Signed and Sealed this

Twenty-first Day of December, 2010

David J. Kappos
*Director of the United States Patent and Trademark Office*